United States Patent
Tamura et al.

(10) Patent No.: US 11,160,633 B2
(45) Date of Patent: Nov. 2, 2021

(54) MEDICAL OBSERVATION APPARATUS, DRIVING CONTROL METHOD, MEDICAL OBSERVATION SYSTEM, AND SUPPORT ARM APPARATUS

(71) Applicants: SONY OLYMPUS MEDICAL SOLUTIONS INC., Tokyo (JP); SONY CORPORATION, Tokyo (JP)

(72) Inventors: Shigeru Tamura, Tokyo (JP); Yasuhiro Matsuda, Tokyo (JP)

(73) Assignees: SONY OLYMPUS MEDICAL SOLUTIONS INC., Tokyo (JP); SONY CORPORATION, Tokyo (JP)

( * ) Notice: Subject to any disclaimer, the term of this patent is extended or adjusted under 35 U.S.C. 154(b) by 344 days.

(21) Appl. No.: 16/080,226

(22) PCT Filed: Mar. 10, 2017

(86) PCT No.: PCT/JP2017/009649
§ 371 (c)(1),
(2) Date: Aug. 27, 2018

(87) PCT Pub. No.: WO2017/169649
PCT Pub. Date: Oct. 5, 2017

(65) Prior Publication Data
US 2019/0015175 A1    Jan. 17, 2019

(30) Foreign Application Priority Data
Mar. 28, 2016   (JP) .............................. JP2016-063688

(51) Int. Cl.
*A61B 90/50*      (2016.01)
*A61B 1/00*       (2006.01)
(Continued)

(52) U.S. Cl.
CPC .......... *A61B 90/50* (2016.02); *A61B 1/00006* (2013.01); *A61B 1/00149* (2013.01);
(Continued)

(58) Field of Classification Search
CPC ......... A61B 90/50; A61B 34/30; A61B 90/25; A61B 90/361; A61B 90/37;
(Continued)

(56) References Cited

U.S. PATENT DOCUMENTS 5,693,043 A * 12/1997 Kittrell .............. A61B 1/00096
606/15
5,971,976 A * 10/1999 Wang ..................... A61B 34/35
606/1
(Continued)

FOREIGN PATENT DOCUMENTS

| JP | 08-197482 A | 8/1996 |
|----|----|----|
| WO | WO 2015/046081 A1 | 4/2015 |
| WO | WO 2015/146850 A1 | 10/2015 |

OTHER PUBLICATIONS

International Search Report dated Jun. 13, 2017, in PCT/JP2017/009649, filed Mar. 10, 2017.

*Primary Examiner* — Timothy J Neal
*Assistant Examiner* — William B Chou
(74) *Attorney, Agent, or Firm* — Xsensus LLP

(57) ABSTRACT

A medical observation apparatus includes an imaging device that captures an observation target, an arm that supports the imaging device and includes multiple links joined to each other by multiple joints, and driving circuitry. The driving circuitry is configured to determine a control torque in at least one joint to be controlled from among the multiple joints and to control driving of the at least one joint based on
(Continued)

the control torque such that an external torque acting on the at least one joint according to an operation on the arm is within a fixed range.

20 Claims, 10 Drawing Sheets

(51) Int. Cl.

| | | |
|---|---|---|
| *G02B 21/32* | (2006.01) | |
| *A61B 90/25* | (2016.01) | |
| *G03B 15/14* | (2021.01) | |
| *G02B 21/00* | (2006.01) | |
| *A61B 34/30* | (2016.01) | |
| *A61B 90/00* | (2016.01) | |
| *B25J 9/16* | (2006.01) | |
| *G05B 19/042* | (2006.01) | |
| *A61B 34/20* | (2016.01) | |
| *G03B 17/56* | (2021.01) | |

(52) U.S. Cl.
CPC .......... *A61B 1/00188* (2013.01); *A61B 34/30* (2016.02); *A61B 90/25* (2016.02); *A61B 90/361* (2016.02); *A61B 90/37* (2016.02); *B25J 9/1633* (2013.01); *B25J 9/1641* (2013.01); *B25J 9/1651* (2013.01); *B25J 9/1697* (2013.01); *G02B 21/0012* (2013.01); *G02B 21/32* (2013.01); *G03B 15/14* (2013.01); *A61B 2034/2059* (2016.02); *A61B 2090/061* (2016.02); *A61B 2090/064* (2016.02); *A61B 2090/066* (2016.02); *A61B 2090/371* (2016.02); *A61B 2090/372* (2016.02); *A61B 2090/502* (2016.02); *G03B 17/561* (2013.01); *G05B 19/042* (2013.01); *G05B 2219/2652* (2013.01); *G05B 2219/39237* (2013.01); *G05B 2219/40599* (2013.01); *G05B 2219/40613* (2013.01); *G05B 2219/45169* (2013.01)

(58) Field of Classification Search
CPC ............ A61B 1/00006; A61B 1/00149; A61B 1/00188; A61B 2034/2059; A61B 2090/061; A61B 2090/064; A61B 2090/066; A61B 2090/371; A61B 2090/372; A61B 2090/502; B25J 9/1633; B25J 9/1641; B25J 9/1651; B25J 9/1697; G02B 21/0012; G02B 21/32; G03B 15/14; G03B 17/561; G05B 19/042; G05B 2219/2652; G05B 2219/39237; G05B 2219/40599; G05B 2219/40613; G05B 2219/45169

See application file for complete search history.

(56) References Cited

U.S. PATENT DOCUMENTS

| | | |
|---|---|---|
| 6,204,620 B1 | 3/2001 | McGee et al. |
| 6,313,595 B2 | 11/2001 | Swanson et al. |
| 2004/0106916 A1* | 6/2004 | Quaid .................. A61B 34/76 606/1 |
| 2007/0142823 A1* | 6/2007 | Prisco .................. A61B 34/70 606/1 |
| 2010/0217082 A1* | 8/2010 | Ito ........................ A61B 1/0055 600/121 |
| 2010/0286791 A1* | 11/2010 | Goldsmith ......... A61B 17/0057 623/23.7 |
| 2013/0165908 A1* | 6/2013 | Purdy ................ A61B 1/00149 606/1 |
| 2015/0250547 A1* | 9/2015 | Fukushima ............ B25J 9/1697 606/130 |
| 2016/0365771 A1* | 12/2016 | Kokubo ................ H02K 7/116 |
| 2017/0007336 A1* | 1/2017 | Tsuboi .................. A61B 34/30 |
| 2017/0007342 A1* | 1/2017 | Kasai .................. A61B 90/361 |
| 2017/0014998 A1* | 1/2017 | Langenfeld ............ B25J 9/126 |
| 2017/0066131 A1* | 3/2017 | Kamikawa ............ A61B 34/30 |
| 2017/0080574 A1* | 3/2017 | Kuroda ................ H04N 5/2257 |
| 2018/0021094 A1* | 1/2018 | Matsuda ................ A61B 90/50 600/102 |
| 2018/0036877 A1* | 2/2018 | Kamikawa ............ A61B 90/00 |
| 2018/0042464 A1* | 2/2018 | Arai ...................... A61B 90/00 |
| 2018/0110581 A1* | 4/2018 | Kamata .............. G02B 21/362 |
| 2018/0193102 A1* | 7/2018 | Inoue .................... A61B 1/018 |
| 2020/0268466 A1* | 8/2020 | Zemlok .................. G01L 3/108 |

* cited by examiner

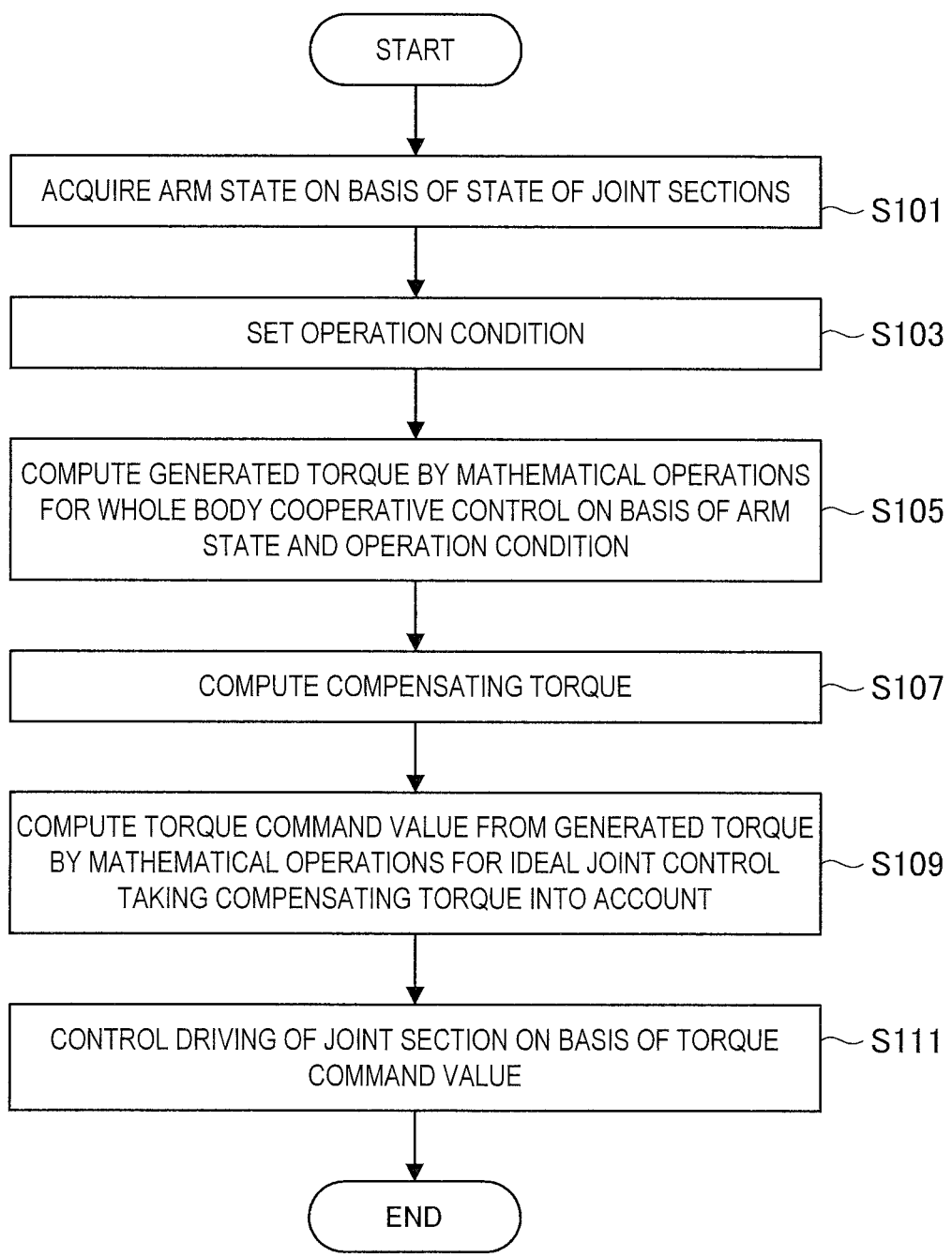

MEDICAL OBSERVATION APPARATUS, DRIVING CONTROL METHOD, MEDICAL OBSERVATION SYSTEM, AND SUPPORT ARM APPARATUS

TECHNICAL FIELD

The present disclosure relates to a medical observation apparatus, a driving control method, a medical observation system, and a support arm apparatus.

BACKGROUND ART

Recently, in the medical field, support arm apparatus are being used to support surgeries. For example, a method is proposed in which an observation section for observing a surgical site, such as a microscope section or an endoscope, is provided on the front end of an arm section of a support arm apparatus, and a surgeon performs surgery while observing the surgical site. Alternatively, there is also proposed a method in which a treatment tool, such as forceps or a retractor, is provided on the front end of the arm section, and the support arm apparatus is made to support or perform operations with the treatment tool which have been performed manually in the past. Note that in the following description, an observation section, treatment tool, and the like provided on the front end of an arm section are collectively designated medical tools. Also, in the following description, a support arm apparatus in which an observation section is provided on the front end of an arm section is also called an observation apparatus.

In such a support arm apparatus, a technology has been proposed in which actuators are provided in each joint section of the arm section, and by driving these actuators, the motion of the arm section is controlled. For example, Patent Literature 1 discloses a technology in a support arm apparatus (that is, an observation apparatus) in which an electronic imaging microscope section having a function of capturing an enlarged image of a surgical site is provided on the front end of an arm section, whereby the motion of the arm section is controlled by force control.

Herein, generally, position control and force control are known as controls methods for what is called a robot apparatus including multiple drive shafts. With position control, command values, such as angles, for example, are given to actuators in joint sections, and the driving of the actuators in each joint section is controlled to follow the command values. On the other hand, with force control, the robot apparatus as a whole is given a target value of force to be imparted to a work target, and the generated torque in the actuators in each joint is controlled to achieve the force indicated by the target value. In general, since position control has difficulty accommodating external forces flexibly, position control is commonly called "hard control", and is said to be unsuited to robot apparatus that carry out tasks while performing a variety of physical interactions with the outside world (for example, physical interactions with human beings). On the other hand, since force control can achieve "soft control" with a force order, force control is a control method suited to robot apparatus that perform physical interactions with human beings in particular, and is said to be a control method with more favorable usability.

In the observation apparatus provided with a microscopic observation section as described in Patent Literature 1, when changing the position and the attitude of the microscope section, it may be anticipated that a user such as a surgeon will perform an operation of gripping and moving the microscope section directly with one's hands. In other words, by applying force control to the driving control of an arm section in an observation apparatus provided with a microscope section, like the technology described in Patent Literature 1, it is conceivable that the operability will be improved for such direct operations by the user.

CITATION LIST

Patent Literature

Patent Literature 1: WO 2015/046081

DISCLOSURE OF INVENTION

Technical Problem

Herein, in a support arm apparatus that controls the motion of an arm section by force control, like the technology described in Patent Literature 1, an external force acting on the arm section may be detected, and the driving of actuators provided in each joint section included in the arm section may be controlled such that the arm section moves in accordance with the external force. Consequently, in the case in which an external force not intended by a user acts on the arm section as a disturbance, there is a risk that the motion of the arm section intended by the user will not be achieved, and user operability may be impaired. In the technology described in Patent Literature 1, by taking into account the influence of such a disturbance more specifically, there is a possibility of being able to provide even more favorable operability to the user.

Accordingly, the present disclosure proposes a novel and improved medical observation apparatus, driving control method, medical observation system, and support arm apparatus capable of further improving user operability.

Solution to Problem

According to the present disclosure, there is provided a medical observation apparatus including: an imaging section that captures an observation target to perform magnified observation of the observation target; an arm section that supports the imaging section and includes multiple links joined to each other by joint sections; and a driving control section that, by controlling a generated torque in at least one joint section to be controlled from among the multiple joint sections, controls a driving of the at least one joint section. The driving control section controls the driving of the at least one joint section such that an external torque acting on the at least one joint section according to an operation on the arm section is contained in a fixed range.

In addition, according to the present disclosure, there is provided a driving control method including: controlling, by a processor, a driving of at least one joint section to be controlled by controlling a generated torque in the at least one joint section from among multiple joint sections in an arm section that supports an imaging section that captures an observation target to perform magnified observation of the observation target, the arm section including multiple links joined to each other by the joint sections. The driving of the at least one joint section is controlled such that an external torque acting on the at least one joint section according to an operation on the arm section is contained in a fixed range.

In addition, according to the present disclosure, there is provided a medical observation system including: a medical observation apparatus that captures an observation target;

and a display apparatus that displays an image of the observation target captured by the medical observation apparatus. The medical observation apparatus includes an imaging section that captures an observation target to perform magnified observation of the observation target, an arm section that supports the imaging section and includes multiple links joined to each other by joint sections, and a driving control section that, by controlling a generated torque in at least one joint section to be controlled from among the multiple joint sections, controls a driving of the at least one joint section. The driving control section controls the driving of the at least one joint section such that an external torque acting on the at least one joint section according to an operation on the arm section is contained in a fixed range.

In addition, according to the present disclosure, there is provided a support arm apparatus including: an arm section including multiple links joined to each other by joint sections; and a driving control section that, by controlling a generated torque in at least one joint section to be controlled from among the multiple joint sections, controls a driving of the at least one joint section. The driving control section controls the driving of the at least one joint section such that an external torque acting on the at least one joint section according to an operation on the arm section is contained in a fixed range.

According to the present disclosure, in a support arm apparatus that supports a medical tool with an arm section, particularly in a medical observation apparatus that supports a microscope section, when controlling at least one joint section included in the arm section, the driving of the at least one joint section is controlled such that an external torque acting on the at least one joint section according to an operation on the arm section is contained in a fixed range. Consequently, when a user touches the arm section directly to cause the arm section to move, it is sufficient for the user to supply a force corresponding to an external torque inside the above fixed range, and thus an approximately constant operational feeling can be obtained. Thus, operability for the user can be improved.

Advantageous Effects of Invention

According to the present disclosure as described above, further improvement in operability for the user becomes possible. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 10 is a flowchart illustrating an example of a processing procedure of a driving control method of the observation apparatus according to the first embodiment.

MODE(S) FOR CARRYING OUT THE INVENTION

Figure 1:
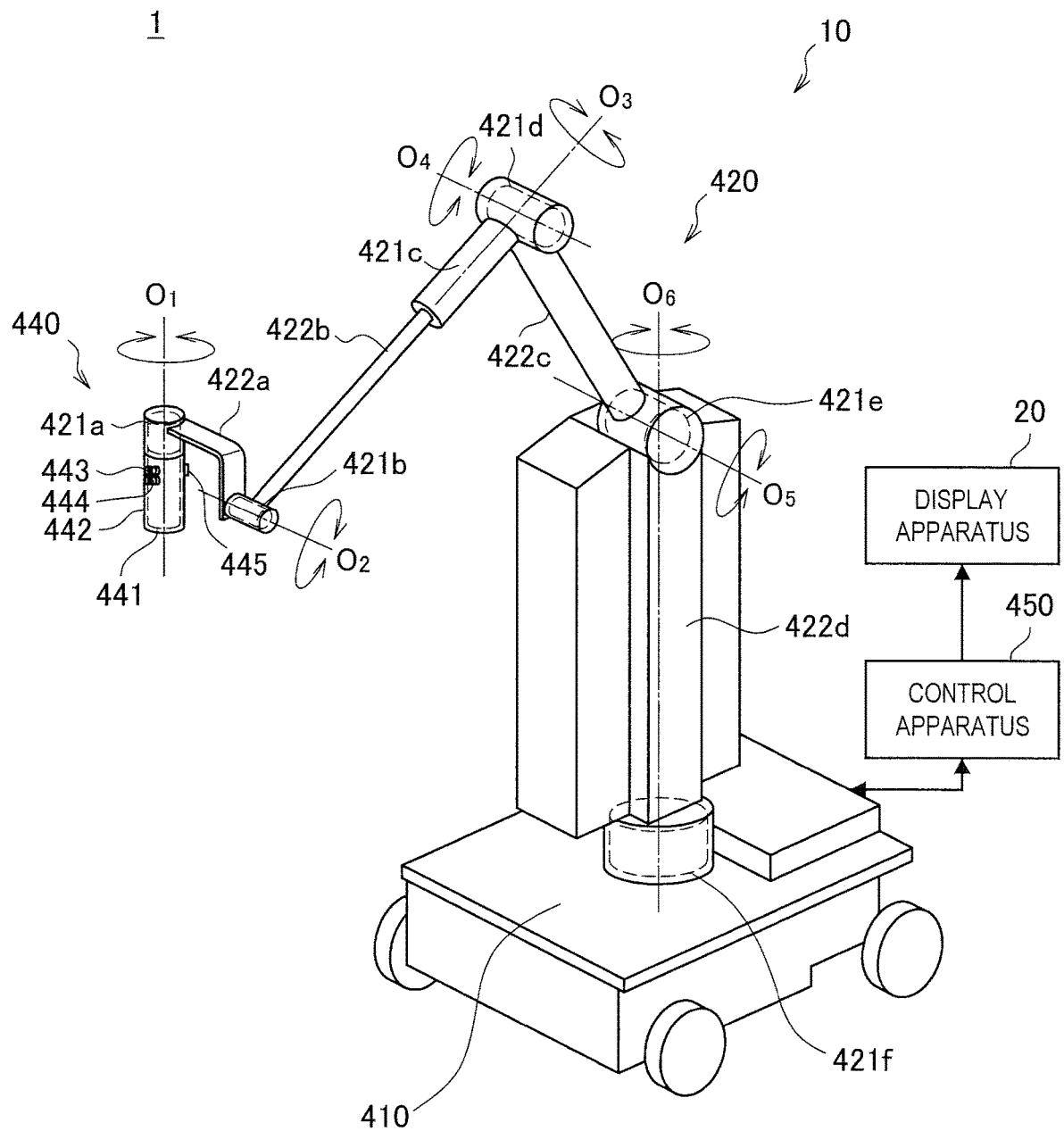
FIG. 1 is a diagram illustrating a configuration of an observation system according to a first embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.

1. First embodiment
  1-1. Configuration of observation system
    1-1-1. Overall configuration
    1-1-2. Configuration of actuator
  1-2. Disturbance caused by rigidity of cable
  1-3. Functional configuration of observation apparatus
  1-4. Driving control method
  1-5. Modifications
2. Second embodiment
  2-1. Background underlying second embodiment
  2-2. Details of second embodiment
  2-3. Modifications
    2-3-1. Magnitude of compensating torque $\tau_c'$
    2-3-2. Combination of first and second embodiments
3. Summary of first and second embodiments
4. Supplement Note that following describes, as one example of the present disclosure, an embodiment in which the support arm apparatus is an observation apparatus in which an electronic imaging microscope section is provided on the front end of the arm section thereof, and surgery is performed using the observation apparatus. However, the present disclosure is not limited to such an example. The technology according to the present disclosure preferably is applied to all types of support arm apparatus, regardless of the type of medical tool supported on the front end of the arm section. Also, the medical procedure to which the technology according to the present disclosure is applied is not limited to surgery, and preferably is any of various types of medical procedures, such as examinations. The technology according to the present disclosure achieves favorable operability in a support arm apparatus, and is capable of exhibiting similar advantageous effects regardless of the type of medical tool supported on the front end of the arm section or the content of the medical procedure to which the technology is applied.

Also, in the following description, a user who uses the observation system described later and a user who operates the observation apparatus described later are designated the surgeon for the sake of convenience. However, this designation does not limit the user who uses the observation system or the user who operates the observation apparatus, and the subject who uses the observation system as well as the subject who operates the observation apparatus may also be another medical staff member, such as an assistant or a nurse.

1. First Embodiment

1-1. Configuration of Observation System

1-1-1. Overall Configuration

The configuration of an observation system according to a first embodiment of the present disclosure, and an observation apparatus that forms the observation system, will be described with reference to FIG. 1. FIG. 1 is a view illustrating a configuration of the observation system according to the first embodiment.

Referring to FIG. 1, the observation system 1 according to the first embodiment includes an observation apparatus 10 that includes a microscope section 440 and captures an image of a surgical site of a patient that is an object to be observed with the microscope section 440, and a display apparatus 20 that displays the image of the surgical site captured by the observation apparatus 10. During surgery, the surgeon observes the surgical site and performs various procedures on the surgical site, while referring to the image captured by the observation apparatus 10 and displayed on the display apparatus 20.

(Display Apparatus)

Under control of a control apparatus 450 of the observation apparatus 10 described later, the display apparatus 20 displays the image of the patient's surgical site captured by the observation apparatus 10. The display apparatus 20 is installed in a location visible to the surgeon in an operating room, such as on a wall of the operating room, for example. The type of the display apparatus 20 is not particularly limited, and any of various publicly known types of display apparatus may be used as the display apparatus 20, such as a cathode ray tube (CRT) display apparatus, a liquid crystal display apparatus, a plasma display apparatus, or an electroluminescence (EL) display apparatus. Additionally the display apparatus 20 is not necessarily required to be installed inside the operating room, and may also be mounted onboard a device used by being worn on the surgeon's body, such as a head-mounted display (HMD) or an eyeglasses-type wearable device.

Note that, as will be described later, in a case in which an imaging section 441 of the microscope section 440 of the observation apparatus 10 is configured as a stereo camera, or such that high-resolution imaging is possible, a display apparatus 20 capable of 3D display or capable of displaying an image with high resolution may be used accordingly.

(Observation Apparatus)

The observation apparatus 10 is equipped with a microscope section 440 for performing magnified observation of the patient's surgical site, an arm section 420 that supports the microscope section 440, a base section 410 to which one end of the arm section 420 is connected and which supports the microscope section 440 and the arm section 420, and the control apparatus 450 that controls the operation of the observation system 1 and the observation apparatus 10.

(Base Section)

The base section 410 is the base of the observation apparatus 10, and the arm section 420 extends from the base section 410. The base section 410 is provided with casters, and thus the observation apparatus 10 contacts the floor through the casters, and is movable across the floor by the casters. However, the configuration of the observation apparatus 10 according to the first embodiment is not limited to such an example, and for example, the observation apparatus 10 may be configured such that the base section 410 is not provided, and the arm section 420 is attached directly to the ceiling or a wall of the operating room. For example, in the case in which the arm section 420 is attached to the ceiling, the observation apparatus 10 is configured such that the arm section 420 hangs down from the ceiling.

(Microscope Section)

The microscope section 440 includes a microscope body for performing magnified observation of a surgical site of a patient. In the illustrated example, the optical axis direction of the microscope section 440 is approximately aligned with the vertical direction. The microscope section 440 has a configuration corresponding to an electronic imaging microscope, and includes a barrel section 442 having an approximately cylindrical shape, and an imaging section 441 provided inside the barrel section 442. The imaging section 441 includes an optical system and an image sensor. The optical system includes optical elements such as a zoom lens, a focus lens, or other lenses, and a mirror. The image sensor captures an image of an observation target, namely the surgical site, with light transmitted through the optical system.

The aperture on the bottom end of the barrel section 442 is provided with a cover glass for protecting the imaging section 441. A light source is also provided inside the barrel section 442, and during image capture, a subject is irradiated with illuminating light radiating from the light source through the cover glass. Of this illuminating light, the light reflecting back from the subject (observation light) is incident on the imaging section 441 via the cover glass, and as a result, a signal relating to the image of the subject (video signal) is acquired by the imaging section 441.

For the imaging section 441, it is sufficient to apply a configuration implemented in any of various publicly known types of electronic imaging microscope sections, and for this reason a detailed description thereof will be reduced or omitted herein. For example, any of various publicly known types of image sensors may be applied as the image sensor of the imaging section 441, such as a charge-coupled device (CCD) sensor or a complementary metal-oxide-semiconductor (CMOS) sensor. Additionally, the imaging section 441 may also be configured as a stereo camera equipped with a pair of image sensors. Also, any of various publicly known types of configurations may be applied to the optical system of the imaging section 441. Furthermore, any of various types of functions typically provided in electronic imaging microscope sections, such as an autofocus (AF) function and an optical zoom function, may be provided onboard the imaging section 441.

Also, the imaging section 441 may be configured such that high-resolution imaging, such as 4K or 8K imaging, for example, is possible. Having the imaging section 441 be configured such that high-resolution imaging is possible enables an image to be displayed on the display apparatus 20 with a large screen of 50 inches or more, for example, while ensuring a predetermined resolution (for example, Full HD image quality), so visibility by the surgeon improves. Also, the predetermined resolution is able to be ensured even when an image is displayed after having been suitably magnified by an electronic zoom function. Therefore, there is no longer a need for the optical zoom function in the microscope section 440, so the optical system of the microscope section 440 is able to be simpler. Consequently, the microscope section 440 can be made smaller.

The video signal acquired by the microscope section 440, that is video data, is transmitted to the control apparatus 450. Various kinds of image processing, such as gamma correction, white balance adjustment, and magnification and inter-pixel correction relating to the electronic zoom function and the like, for example, are performed on the video data in the control apparatus 450. With this image processing, various kinds of image processing typically performed to display an image may be performed. The video data that has undergone the various kinds of image processing is transmitted to the display apparatus 20 provided in the operating room, and a video of the surgical site is appropriately magnified at the desired magnification by the optical zoom function and/or the electronic zoom function, for example, and displayed on the display apparatus 20. Note that communication between the control apparatus 450 and the display apparatus 20 may be realized by any of various publicly known wired or wireless methods.

Note that the above image processing does not necessarily have to be executed by the control apparatus 450. For example, a processing circuit for executing the above image processing may also be provided in the microscope section 440. In tins case, image data which has been subjected to appropriate image processing in the processing circuit installed in the microscope section 440 may be transmitted from the microscope section 440 to the display apparatus 20. Also, in this case, the communication between the microscope section 440 and the display apparatus 20 preferably is realized by any of various publicly known wired or wireless methods.

The microscope section 440 is provided with various types of switches for controlling the operation of the microscope section 440. For example, the microscope section 440 is provided with a zoom switch 443 (zoom SW 443) and a focus switch 444 (focus SW 444) for adjusting the image capture parameters of the microscope section 440, as well as an operating mode toggle switch 445 (operating mode toggle SW 445) for toggling the operating mode of the arm section 420.

The surgeon, by operating the zoom SW 443 and the focus SW 444, is able to adjust the magnification and the focal length of the microscope section 440, respectively. Also, by operating the operating mode toggle SW 445, the surgeon is able to toggle the operating mode of the arm section 420 between a locked mode and a free mode.

Herein, the locked mode is an operating mode in which the position and the attitude of the microscope section 440 are locked by using a brake to restrain rotation about each rotation axis provided in the arm section 420. The free mode is an operating mode in which the brake is released, thereby allowing free rotation about each rotation axis provided in the arm section 420. For example, in the free mode, it is possible to adjust the position and the attitude of the microscope section 440 with direct operations by the surgeon. Herein, direct operations mean operations in which the surgeon grips the microscope section 440 with his or her hand, for example, and directly moves the microscope section 440. For example, the operating mode of the arm section 420 becomes the free mode while the surgeon is pressing the operating mode toggle SW 445, and the operating mode of the arm section 420 becomes the locked mode while the surgeon releases his or her hand from the operating mode toggle SW 445.

Note that these switches are not necessarily required to be provided on the microscope section 440. In the first embodiment, it is sufficient for the observation apparatus 10 to be provided with a mechanism for accepting operating input having functions similar to these switches, and the specific configuration of such a mechanism is not limited. For example, these switches may also be provided on another section of the observation apparatus 10. As another example, an input apparatus such as a remote control, a foot switch or the like may be used, and commands corresponding to these switches may be input into the observation apparatus 10 remotely.

Also, although the barrel section 442 of the microscope section 440 is illustrated as a simple cylindrically-shaped member in FIG. 1 for the sake of simplicity, the barrel section 442 may also be provided with a grip section gripped by the surgeon. Such a grip section may be realized by having a structure such as a handle to be gripped by the surgeon be formed around the outer circumference of the barrel section 442. Alternatively, such a grip section may be realized by having the shape of the barrel section 442 be formed into a shape that is gripped easily by the surgeon. For example, as described above, when in the free mode, operations of moving the microscope section 440 with the surgeon gripping the barrel section 442 directly in hand may be anticipated. At this point, since the surgeon performs an operation of moving the microscope section 440 while pressing the operating mode toggle SW 445, the shape of the barrel section 442 and the placement of the operating mode toggle SW 445 may be determined appropriately with consideration for operability by the surgeon while in the free mode. In addition, the placement of the zoom SW 443 and the focus SW 444 may be determined appropriately with similar consideration for operability by the surgeon.

(Arm Section)

The arm section 420 moves the microscope section 440 three-dimensionally, while also securely supporting the position and the attitude of the microscope section 440 after moving. Specifically, the arm section 420 includes multiple joint sections 421a, 421b, 421c, 421d, 421e, 421f, and multiple links 422a, 422b, 422c, 422d rotatably joined to each other by the joint sections 421a to 421e. The arm section 420 is provided with six rotation axes (first axis $O_1$, second axis $O_2$, third axis $O_2$, fourth axis $O_4$, fifth axis $O_5$, and sixth axis $O_6$) corresponding to these six joint sections 421a to 421f, and six degrees of freedom are realized with respect to the moving of the microscope section 440.

The links 422a to 422d are approximately rod-shaped members, in which one end of the link 422d is joined to the base section 410 via the joint section 421f, the other end of the link 422a is joined to one end of the link 422c via the joint section 421e, and additionally, the other end of the link 422c is joined to one end of the link 422b via the joint sections 421d and 421c. Furthermore, the other end of the link 422b is joined to one end of the approximately L-shaped link 422a via the joint section 421b, while the other end of the link 422a and the microscope section 440 are joined via the joint section 421a. In this way, the base section 410 acts as a fulcrum, and the ends of the multiple links 422a to 422d are joined to each other by the joint sections 421a to 421f, thereby configuring an arm shape extending from the base section 410.

The joint sections 421a to 421f are each provided with an actuator 430 illustrated in FIG. 2 to be described later, and the joint sections 421a to 421f are configured to be rotatable about a certain rotation axis according to the driving of the actuator 430. The driving of the actuator 430 is controlled by the control apparatus 450. By respectively controlling the driving of the actuator 430 in each of the joint sections 421a to 421f driving of the arm section 420 is controlled so as to extend or contract (fold up) the arm section 420, for example.

Specifically, by controlling rotation about the first axis $O_1$, rotation about the optical axis of the microscope section 440 is controlled. Also, by controlling each of rotation about the second axis $O_2$ and third axis $O_2$, the direction of the optical axis of the microscope section 440 with respect to the horizontal plane is controlled. In this way, the first axis $O_1$, the second axis $O_2$, and the third axis $O_2$ on the front end side may be considered to be the rotation axes that primarily may control the attitude (the direction of the optical axis) of the microscope section 440. In other words, by controlling the rotation of the joint sections 421a to 421c corresponding to these rotation axes, primarily the attitude of the microscope section 440 may be controlled. On the other hand, the fourth axis $O_4$, the fifth axis $O_5$, and the sixth axis $O_6$ on the root side may be considered to be the rotation axes that primarily may control the three-dimensional position of the microscope section 440. In other words, by controlling the rotation of the joint sections 421d to 421f corresponding to these rotation axes, primarily the position of the microscope section 440 may be controlled.

Note that in the illustrated example, as above, the arm section 420 is configured such that six degrees of freedom are realized with respect to the driving of the microscope section 440. By configuring the arm section 420 to have six degrees of freedom, the microscope section 440 can be moved freely within the movable range of the arm section 420. With this arrangement, the microscope section 440 can be made to take an arbitrary position and attitude, making it possible to observe the surgical site from a variety of angles. However, in the first embodiment, the configuration of the arm section 420 is not limited to the illustrated example. It is sufficient for the arm section 420 to be configured such that the microscope section 440 is able to move appropriately according to the use, while the numbers of the joint sections 421a to 421f and the links 422a to 422d, their arrangement, the directions of the drive shafts of the joint sections 421a to 421f and the like may be set appropriately such that the aft section 420 has the desired degrees of freedom.

(Control Apparatus)

The control apparatus 450 includes a processor such as a central processing unit (CPU) or a digital signal processor (DSP), or a control board or the like on which these processors and a storage element such as memory are mounted together. As a result of a processor included in the control apparatus 450 executing computational processing in accordance with a predetermined program, each function in the control apparatus 450 is realized.

In the first embodiment, force control is used as the control method of the observation apparatus 10. With force control, the force acting on the arm section 420 is detected by a torque sensor of the actuators 430 provided in each of the joint sections 421a to 421f. On the basis of the detected force, a generated torque that needs to be generated by the actuators 430 provided in each of the joint sections 421a to 421f in order for the arm section 420 to perform a desired movement is computed, and this computed generated torque is used as a control value to control the movement of the arm section 420.

For example, with force control, the driving of the actuators 430 may be controlled and the movement of the arm section 420 may be controlled by the control apparatus 450 in response to a direct operation by the surgeon, that is, an operation in which the surgeon touches the arm section 420 and/or the microscope section 440 directly to move the arm section 420 and/or the microscope section 440, such that the arm section 420 moves in the direction of the force imparted to the arm section 420 (in other words, to support the operation by the surgeon). In this way, by using force control, the surgeon is able to move the arm section 420 and/or the microscope section 440 while touching the arm section 420 and/or the microscope section 440 directly, thereby making easier and more intuitive operations possible.

Herein, in the first embodiment, a cable that extends along the arm section 420 is provided inside the arm section 420. The cable may fulfill a role of acting as a light guide from a light source apparatus (not illustrated) to the microscope section 440, a role of transmitting image data as well as signals and the like for operating input with respect to a switch from the microscope section 440 to the control apparatus 450, a role of transmitting signals and the like for driving control (for example, driving control of the optical system for changing the magnification and the focal length) of the microscope section 440 from the control apparatus 450 to the microscope section 440, a role of transmitting signals for detected rotational angles and torques from the actuators 430 provided in each of the joint sections 421a to 421f of the arm section 420 to the control apparatus 450, a role of transmitting signals for driving control of the actuator 430 from the control apparatus 450 to the actuators 430 provided in each of the joint sections 421a to 421f of the arm section 420, and the like.

In the first embodiment, during the above driving control of the arm section 420 (that is, driving control of each of the joint sections 421a to 421f), the control apparatus 450 takes into account the disturbance caused by the rigidity of the cable to compute the generated torque by the actuators 430 provided in each of the joint sections 421a to 421f. Consequently, the surgeon becomes able to perform operations of moving the arm section 420 and/or the microscope section 440 in a state of reduced influence from the disturbance caused by the rigidity of the cable, and therefore a more favorable operational feeling for the surgeon may be achieved. Note that the disturbance caused by the rigidity of the cable will be described in detail in (1-2. Disturbance caused by rigidity of cable) below. Also, a specific method of controlling the arm section 420 will be described in detail in (1-3. Functional configuration of observation apparatus) below.

Note that in the first embodiment, the control apparatus 450 may also control the driving of the arm section 420 on the basis of operating input other than the direct operation by the surgeon described above. For example, in accordance with operating input performed by the surgeon via any of various types of input apparatus such as a footswitch, the control apparatus 450 may control the driving of the actuators 430 provided in each of the joint sections 421a to 421f, and cause the arm section 420 to move. Alternatively, the observation system 1 may be provided with a navigation apparatus that issues instructions related to the movement of the microscope section 440 to the observation apparatus 10. In this case, upon receiving an instruction from the navigation apparatus, the control apparatus 450 may control the driving of the actuators 430 provided in each of the joint sections 421a to 421f, and cause the arm section 420 to move such that the position and the attitude of the microscope section 440 indicated by the instruction are achieved. Note that any of various publicly known types of apparatus used when moving a microscope section in a typical observation apparatus may be used as the input apparatus or the navigation apparatus above.

For example, in the observation system 1, a demand of wanting to move the field of view of the image on the screen of the display apparatus 20 slightly, or alternatively, a demand of wanting to translate the field of view in any direction without changing the up/down/left/right of the image on the screen of the display apparatus 20, may occur. However, in some cases it is difficult to move the microscope section 440 slightly or translate the microscope section 440 in a direction in a horizontal plane by a direct operation. In such cases, by performing driving control of the arm section 420 via an input apparatus or a navigation apparatus like the above, it becomes possible to move the microscope section 440 more accurately to a position where a desired field of view is obtained. Note that in the following description, causing the arm section 420 to move by a direct operation is sometimes called manual movement of the arm section 420, while causing the arm section 420 to move by remote operating input via an input apparatus or a navigation apparatus is sometimes called automatic movement of the arm section 420.

Note that in the following description, unless particularly noted otherwise, a simple phrase such as "the surgeon is operating the arm section 420 and/or the microscope section 440" is taken to mean that the surgeon is operating the arm section 420 and/or the microscope section 440 directly.

Additionally, the control apparatus 450 may control various operations in the observation system 1 other than driving control of the arm section 420. For example, the control apparatus 450 includes a function of toggling the operating mode of the arm section 420 described above by controlling the driving of the brakes provided in each of the rotation axis sections of the arm section 420 in response to operating input performed by the surgeon via the above operating mode toggle SW 445. Also, for example, the control apparatus 450 includes a function of appropriately driving the optical system of the imaging section 441 of the microscope section 440 to adjust the magnification and the focal length of the microscope section 440 in response to operating input performed by the surgeon via the above zoom SW 443 and focus SW 444. Also, for example, the control apparatus 450 includes a function of performing various types of image processing on image data acquired by the microscope section 440, and causing the display apparatus 20 to display an image based on the processed image data.

Note that in the illustrated example, the control apparatus 450 is provided as a separate configuration from the microscope section 440, the arm section 420, and the base section 410, however, the first embodiment is not limited to such an example. For example, a processor, a control board, or the like that realizes functions similar to the control apparatus 450 may also be disposed inside the base section 410. Alternatively, by incorporating a processor, a control board, or the like that realizes functions similar to the control apparatus 450 into the microscope section 440 internally, the control apparatus 450 and the microscope section 440 may be configured in an integrated manner. Alternatively, functions similar to the functions of the control apparatus 450 may be realized by a processor or a control board or the like being arranged in each of the joint sections 421a to 421f that form the arm section 420 of the observation apparatus 10, and having these plurality of processors or control boards or the like work together.

The above describes a configuration of the observation system 1 and the observation apparatus 10 with reference to FIG. 1.

1-1-2. Configuration of Actuator

Figure 2:
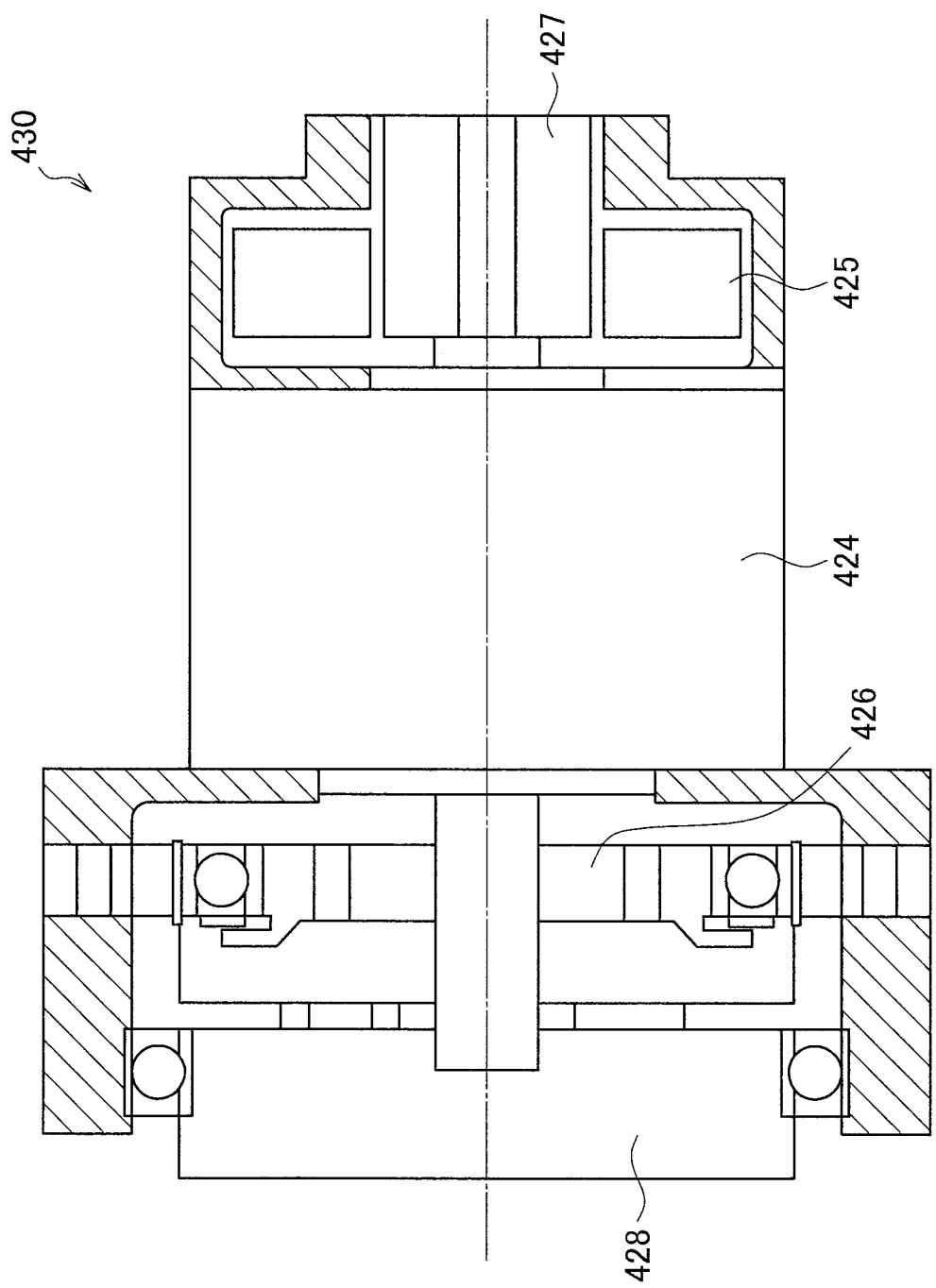
FIG. 2 is a cross-section diagram illustrating an exemplary configuration of an actuator provided in the joint sections of the observation apparatus illustrated in FIG. 1.

FIG. 2 will be referenced to describe a configuration of the actuators provided in the joint sections 421a to 421f of the observation apparatus 10 illustrated in FIG. 1. FIG. 2 is a cross-section diagram illustrating an exemplary configuration of the actuators provided in the joint sections 421a to 421f of the observation apparatus 10 illustrated in FIG. 1. FIG. 2 illustrates a cross-section view of the actuator according to the present embodiment in the case of cutting on a plane that goes through the rotation axis.

Referring to FIG. 2, the actuator 430 according to the first embodiment includes a motor 424, a motor driver 425, a reduction gear 426, an encoder 427, and a torque sensor 428. The actuator 430 is an actuator corresponding to force control. In the actuator 430, the rotation of the motor 424 is reduced by the reduction gear 426 at a predetermined reduction ratio, and transmitted to other members downstream via an output shaft, thereby causing the other members to be driven.

The motor 424 is a driving mechanism that, in a case of being given a certain command value (current command value), causes a rotating shaft to rotate at a rotational velocity corresponding to the command value, and thereby produces driving force. For the motor 424, a brushless motor is used, for example. However, the first embodiment is not limited to such an example, and any of various publicly known types of motors may be used as the motor 424.

The motor driver 425 is a driver circuit (driver integrated circuit (IC)) that rotationally drives the motor 424 by supplying current to the motor 424, and is able to control the rotation rate of the motor 424 by adjusting the amount of current supplied to the motor 424. The motor driver 425 drives the motor 424 by supplying the motor 424 with a current corresponding to the torque command value $\tau$ illustrated in FIG. 9 described later.

The reduction gear 426 is joined to the rotating shaft (drive shaft) of the motor 424. The reduction gear 426 reduces by a certain reduction ratio the rotational velocity of the rotating shaft of the joined motor 424 (in other words, the rotational velocity of the input shaft), and transmits to the output shaft. In the first embodiment, the configuration of the reduction gear 426 is not limited to a specific configuration, and any of various publicly known types of reduction gears may be used as the reduction gear 426. However, for the reduction gear 426, it is preferable to use one capable of accurately setting the reduction ratio, such as a Harmonic Drive (registered trademark), for example. In addition, the reduction ratio of the reduction gear 426 may be set appropriately according to the application of the actuator 430. For example, in the case of applying the actuator 430 to the joint sections 421a to 421f of the observation apparatus 10 as in the first embodiment, a reduction gear 426 having a reduction ratio of approximately 1:100 may be used favorably.

The encoder 427 detects the rotational angle of the input shaft (that is, the rotational angle of the rotating shaft of the motor 424). On the basis of the rotation rate of the input shaft detected by the encoder 427, and the reduction ratio of the reduction gear 426, information such as the rotational angle, the rotational angular velocity, and the rotational angular acceleration of the joint sections 421a to 421f may be obtained. For the encoder 427, any of various publicly known types of rotary encoders, such as a magnetic encoder or an optical encoder, for example, may be used. Note that in the illustrated example, the encoder 427 is provided only on the input shaft of the actuator 430, but an encoder for detecting the rotational angle of the output shaft of the actuator 430 additionally may be provided farther downstream than the reduction gear 426.

The torque sensor 428 is connected to the output shaft of the actuator 430, and detects the torque acting on the actuator 430. The torque sensor 428 detects the torque output by the actuator 430 (generated torque). Additionally, the torque sensor 428 is also able to detect external torque imparted to the actuator 430 from the outside (for example, torque imparted from the outside by the surgeon in a direct operation).

The above describes a configuration of the actuator 430 according to the first embodiment with reference to FIG. 2. In the case in which force control is performed, in the observation apparatus 10, the rotational angle of each of the joint sections 421a to 421f and the torque acting on each of the joint sections 421a to 421f are detected respectively by the encoder 427 and the torque sensor 428 provided in each actuator 430. At this time, the torque acting on each of the joint sections 421a to 421f detected by the torque sensor 428 may also include force acting on the arm section 420 and/or the microscope section 440. The detected rotational angles and torque values are transmitted to the control apparatus 450 through the cable that extends inside the arm section 420 described above. Additionally, on the basis of the detected rotational angles and torque values, a torque that needs to be generated by the actuators 430 of each of the joint sections 421a to 421f in order for the arm section 420 to achieve a desired operation is computed by the control apparatus 450, and this torque is used as a control value to drive the actuators 430 of each the joint sections 421a to 421f.

Note that the configuration illustrated in FIG. 2 merely illustrates one exemplary configuration of the actuator 430 according to the first embodiment, and the first embodiment is not limited to such an example. For the actuator 430, it is possible to use any of various publicly known types of actuators typically used in an apparatus whose movement is controlled by force control.

1-2. Disturbance Caused by Rigidity of Cable

FIGS. 3 to 6 will be referenced to describe the disturbance caused by the rigidity of the cable. Note that in the first embodiment, the disturbance caused by the rigidity of the cable in the joint sections whose rotation axis functions as a torsion rotation axis parallel to the extension direction of a link connected to itself (that is, causes a link connected to itself to rotate about a rotation axis parallel to the extension direction of the link) from among the joint sections 421a to 421f included in the arm section 420 is targeted for reduction. In the case of the configuration illustrated in FIG. 1, the joint section 421a corresponding to the first axis $O_1$, joint section 421c corresponding to the third axis $O_3$, and the joint section 421f corresponding to the sixth axis $O_6$ correspond to torsion joint sections. Herein, as one example, the disturbance caused by the rigidity of the cable in the driving control of the joint section 421c illustrated in FIG. 1 will be described.

Figure 3:
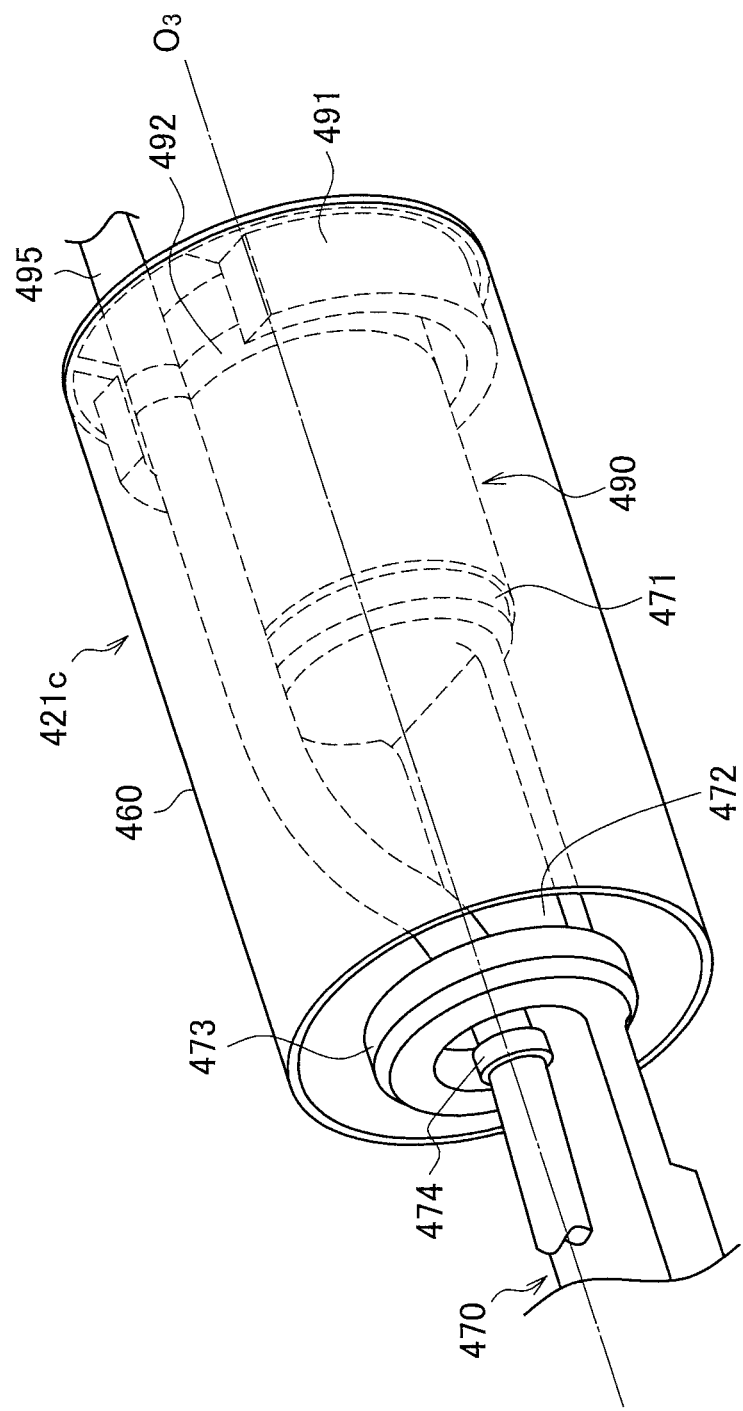
FIG. 3 is a diagram illustrating an extraction of the configuration near the joint section 421c illustrated in FIG. 1.
Figure 4:
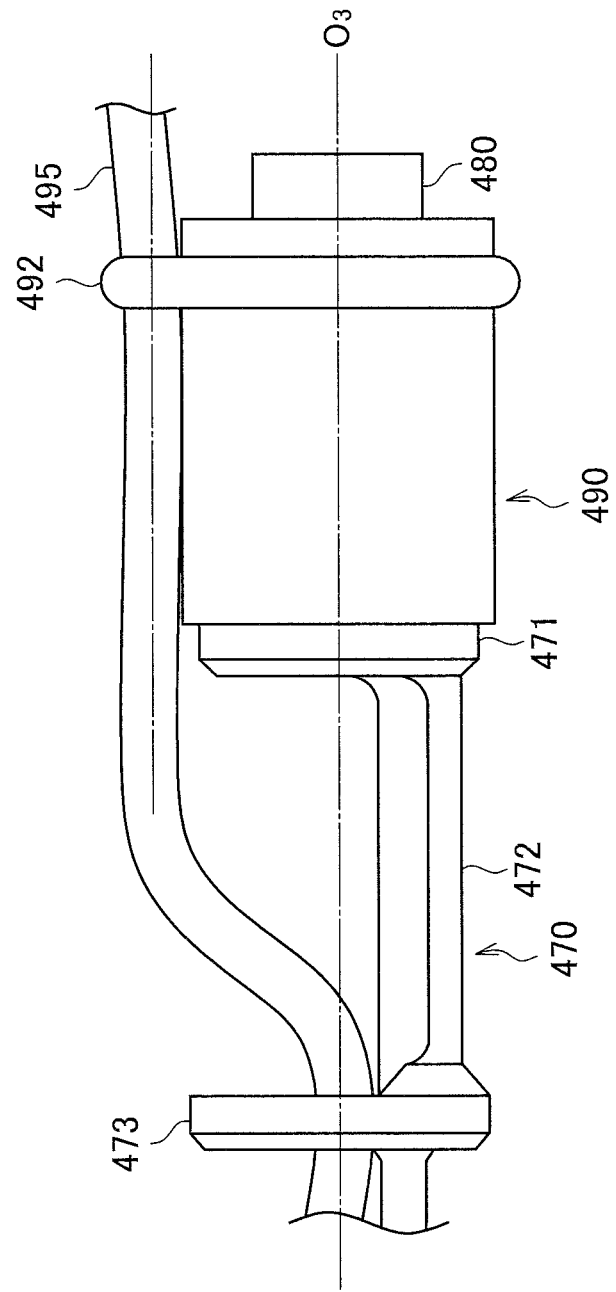
FIG. 4 is a diagram illustrating an extraction of the configuration near the joint section 421c illustrated in FIG. 1.
Figure 5:
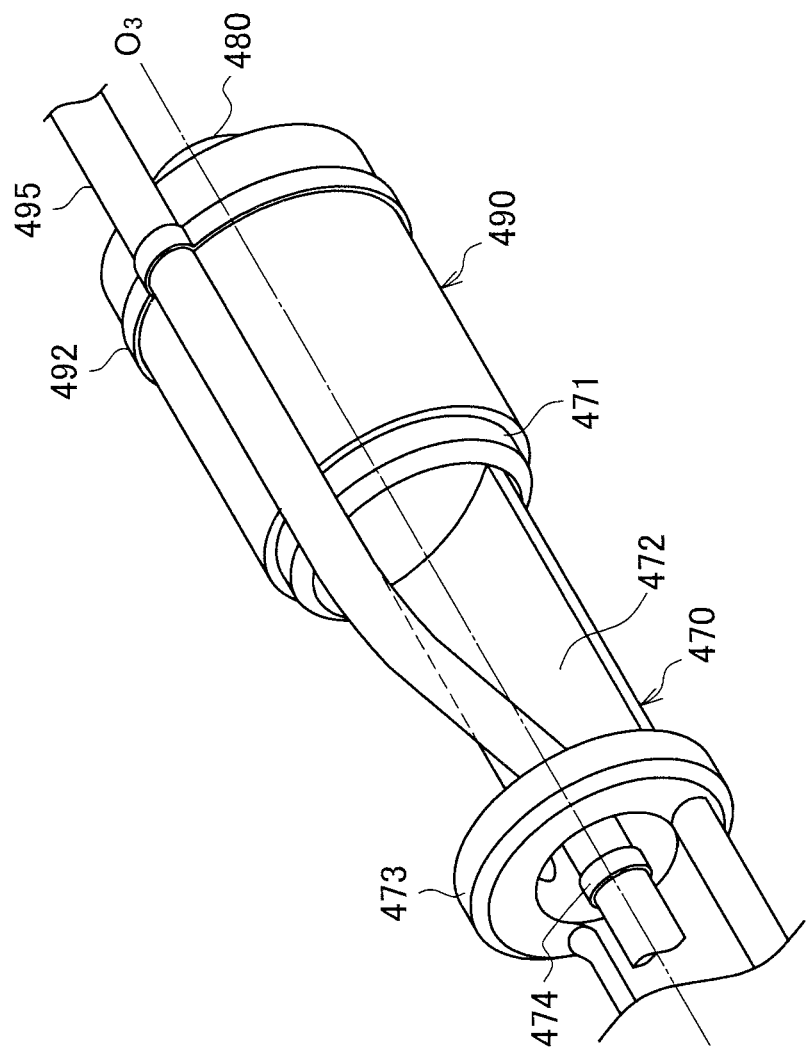
FIG. 5 is a diagram illustrating an extraction of the configuration near the joint section 421c illustrated in FIG. 1.
Figure 6:
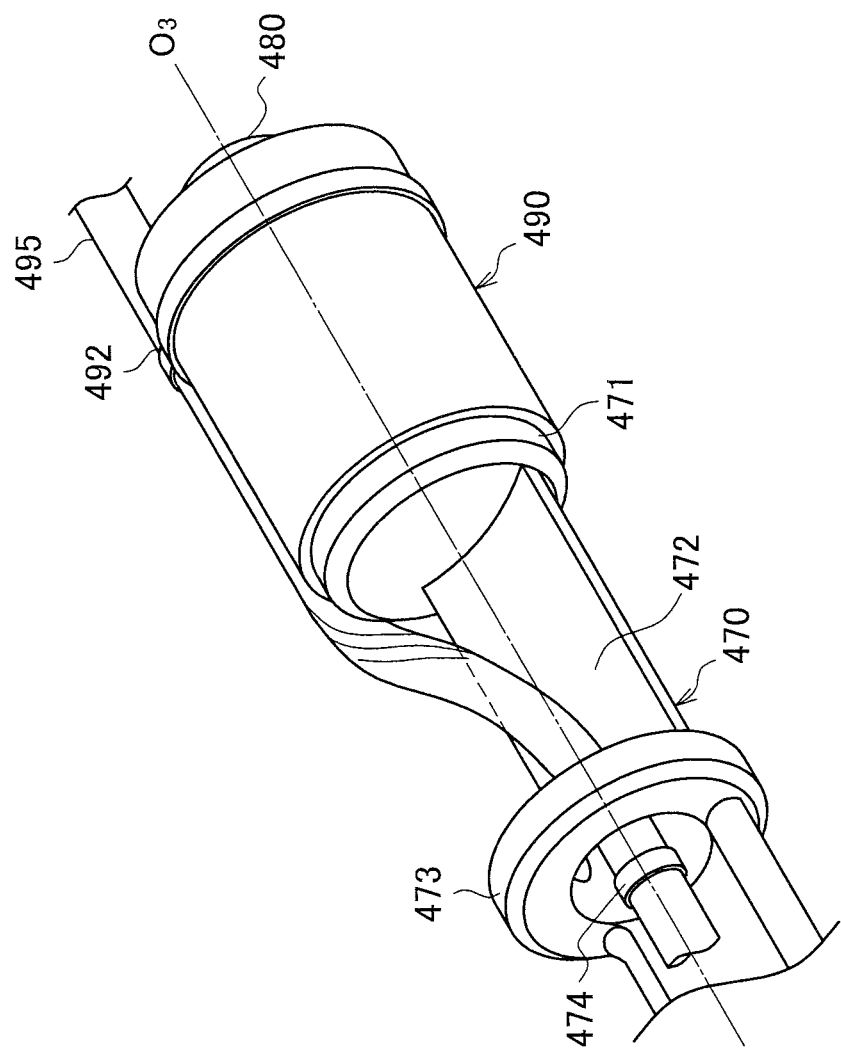
FIG. 6 is a diagram illustrating an extraction of the configuration near the joint section 421c illustrated in FIG. 1.

FIGS. 3 to 6 are diagrams illustrating an extraction of the configuration near the joint section 421c illustrated in FIG. 1. FIG. 3 is a perspective view of the joint section 421c, while FIG. 4 is a side view illustrating a state in which a cover 460 and a joining member 491 described later have been removed from the joint section 421c, and FIG. 5 is a perspective view illustrating a state in which the cover 460 and the joining member 491 described later have been removed from the joint section 421c. FIG. 6 is a perspective view illustrating a state in which the joint section 421c has rotated from the state illustrated in FIG. 5. Note that FIGS. 3 to 6 illustrate a single cable 495 in a representative manner, but in actuality, multiple cables may be bundled and extended inside the joint section 421c (that is, inside the arm section 420).

Here, FIGS. 3 to 5 illustrate a state in which a torsional load is not imparted to the cable 495. The state in which a torsional load is not imparted referred to herein refers to a state in which the central axis of the cable 495 (in the case in which the cable 495 is a bundling of multiple cables, the axis passing through the center of gravity in a cross-section) is in a plane that passes through the rotation axis (the third axis $O_3$) of the joint section 421c. In the first embodiment, the joint section 421c is configured such that in the state in which the joint section 421c is not rotated, that is, in the case in which the rotational angle of the joint section 421c is zero, the central axis of the cable 495 is positioned in the plane that passes through the rotation axis (O3 axis) of the joint section 421c, and therefore the state in which a torsional load is not imparted may mean a state in which the rotational angle of the joint section 421c is zero. On the other hand, FIG. 6 illustrates a state in which the joint section 421d is rotated from the state illustrated in FIG. 5 as above, or in other words, a state in which a torsional load is imparted to the cable 495.

Referring to FIGS. 3 to 5, the joint section 421c includes a cover 460 which has a tubular shape and which is attached to the link 422b illustrated in FIG. 1 on the front end side, an extending section 470 that extends towards the joint section 421d illustrated in FIG. 1, a rotation axis section 480 which is provided on the end on the opposite side of the side where the extending section 470 is connected to the joint section 421d and whose central axis is aligned with the third axis $O_3$, and a rotating section 490 which is rotatable about the rotation axis section 480.

The extending section 470 includes a disc-shaped fixed section 471 that is affixed to the rotation axis section 480, a planar joining section 472 which is joined to the fixed section 471 and which connects the fixed section 471 and the joint section 421d, and a guide section 473 which forms a C-shape and whose open end is affixed to the joining section 472, and which forms a midair space through which the cable 495 can be inserted and guided. The joining section 472 extends to form a planar shape along the third axis $O_3$.

The rotating section 490 is connected to the drive shaft of the actuator 430, and rotates about the rotation axis section 480 in association with the driving of the actuator 430. The rotating section 490 is joined to the inner circumferential part of the cover 460 by the joining member 491. For this reason, if the rotating section 490 rotates about the rotation axis section 480, the cover 460 rotates in conjunction with the rotation of the rotating section 490. If the cover 460 rotates, the 422b joined to the cover 460 rotates about the rotation axis section 480, or in other words, the third axis $O_3$.

In the joint section 421c, the cable 495 is affixed to the joining section 472 and the rotating section 490 by bundling bands 474 and 492, respectively. Specifically, the bundling band 474 affixes the cable 495 to the joining section 472 in the midair space of the guide section 473. The bundling band 492 of the cable 495 by connecting the cable 495 and the outer circumference of the rotating section 490. The affixed positions of the cable 495 by the bundling bands 474 and 492 preferably are provided on each of one end and the other end of the third axis O₃ in the joint section 421c.

Note that in the illustrated example, the cable 495 is affixed by the bundling band 474 at a position where the central axis of the cable 495 is approximately aligned with the third axis O₃ in the joining section 472, and is affixed by the bundling band 492 such that the central axis of the cable 495 is positioned at a different position than the third axis O₃ in the rotating section 490. For this reason, the affixed portion of the cable 495 in the joining section 472 and the affixed portion of the cable 495 in the rotating section 490 are in an offset state. Note that a state in which a first part and another part in the extension direction of the cable 495 are offset refers to a state in which the central axis of the cable 495 in the first part and the central axis of the cable 495 in the other part are not positioned on approximately the same line. However, the first embodiment is not limited to such an example, and the cable 495 does not necessarily have to be extended in an offset state. For example, the cable 495 does not have to pass through the guide section 473, and may also be extended in a state of uniformly running along the inner circumferential face of the cover 460 of the joint section 421c.

In this way, in the state in which the cable 495 is extended inside the joint section 421c, consider the case in which the joint section 421c rotates, as illustrated in FIG. 6. In this case, as illustrated in FIG. 6, in association with the rotation of the joint section 421c, the cable 495 moves so as to be twisted. In the cable 495 in this twisted state, because of the rigidity of the cable 495, a restoring force (elastic restoring force) that acts to return to the original state (that is, the state illustrated in FIGS. 3 to 5 in which a torsional load is not imparted) occurs. Since the cable 495 is affixed to the joint section 421d by the bundling bands 474 and 492 as above, the restoring force of the cable 495 may become a disturbance acting in a direction opposing rotation with respect to the joint section 421d.

Consequently, in the case of not taking into account the restoring force of the cable 495, and attempting to control the driving of the joint section 421c to rotate by just a predetermined rotational angle corresponding to an operation by the surgeon, there is a risk that the restoring force will work in a direction impeding rotation, and the desired rotational angle will not be achieved. In this way, since the restoring force works in a direction impeding rotation in the joint section 421c, or in other words, in a direction opposing the operation by the surgeon, operability for the surgeon may be degraded significantly.

In the first embodiment, in the driving control of the joint section 421c, this disturbance caused by the rigidity of the cable 495, that is, the restoring force of the cable 495, is also taken into account to compute the generated torque in the joint section 421d for achieving the desired rotational angle. Consequently, the rotational angle can be controlled with higher precision, making it possible to improve operability for the surgeon.

Note that although the above description takes up the joint section 421c as an example, in the first embodiment, the restoring force of the cable 495 may also act similarly as a disturbance in the driving control of the joint sections 421a and 421f which function as the other torsion joint sections. Consequently, in the driving control of these joint sections 421a and 421f, the restoring force of the cable 495 may be taken into account similarly to compute the generated torque.

Hereinafter, while also describing a functional configuration of the observation apparatus 10, a specific method of this driving control of each of the joint sections 421a, 421c, and 421f that takes the restoring force of the cable 495 into account will be described.

1-3. Functional Configuration of Observation Apparatus

Figure 7:
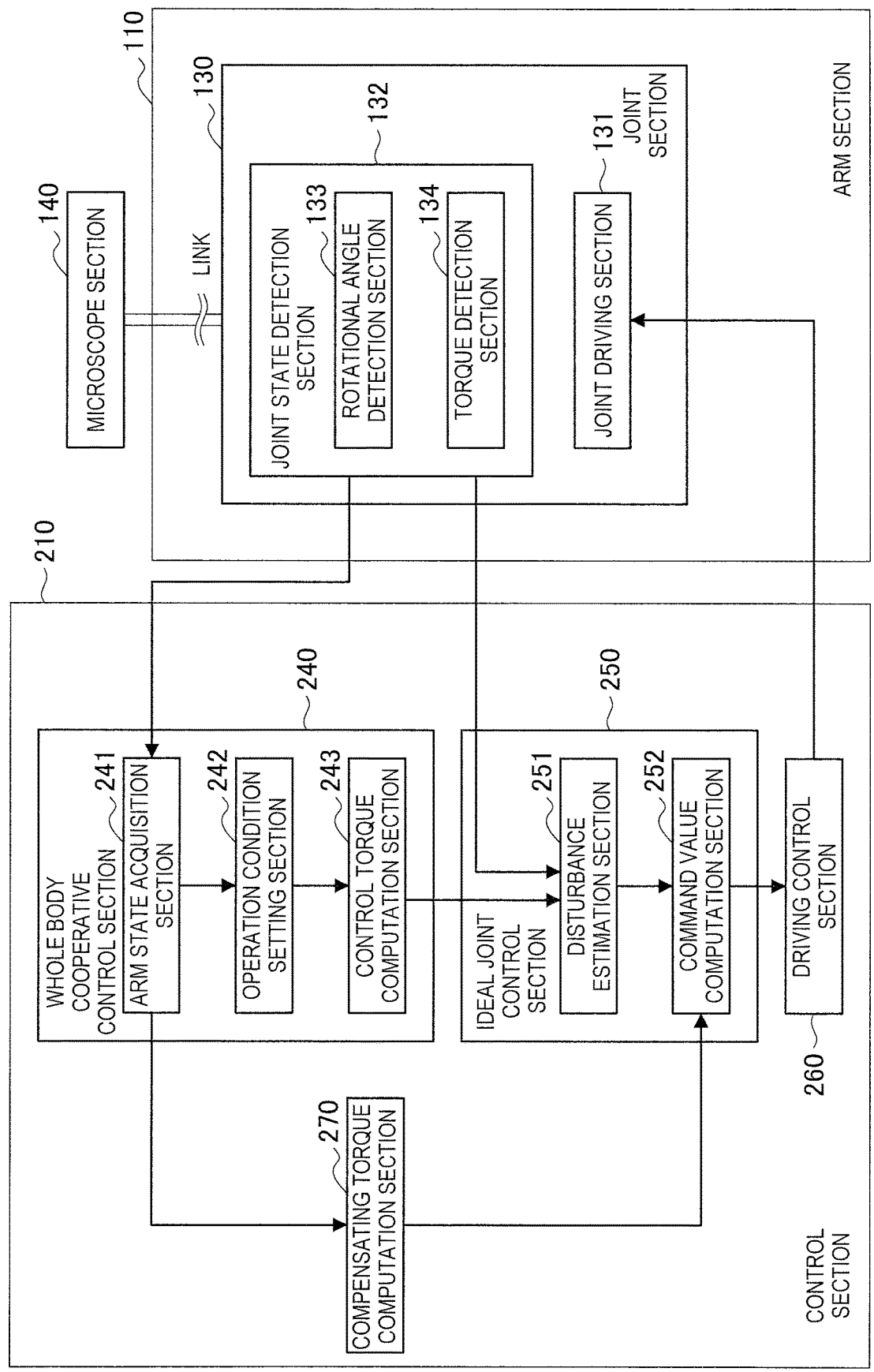
FIG. 7 is a block diagram illustrating an example of a functional configuration of the observation apparatus according to the first embodiment.

FIG. 7 will be referenced to describe a functional configuration of the observation apparatus 10 illustrated in FIG. 1. FIG. 7 is a block diagram illustrating an example of a functional configuration of the observation apparatus 10 according to the first embodiment.

Referring to FIG. 7, the observation apparatus 10 is provided with an arm section 110, a microscope section 140, and a control section 210 as functions thereof. The arm section 110 corresponds to the arm section 420 illustrated in FIG. 1, and the microscope section 140 corresponds to the microscope section 440 illustrated in FIG. 1. Since the functions of the microscope section 140 have already been described with reference to FIG. 1, a description is omitted here.

Note that in actuality, similarly to the configuration illustrated in FIG. 1, the arm section 110 includes multiple links and multiple joint sections, but in FIG. 7, illustrates only the functional configuration of a single joint section 130 in a representative manner. Herein, in the first embodiment, control that takes the disturbance caused by the rigidity of the cable into account is executed only in the driving control of the joint sections 421a, 421c, and 421f that function as torsion joint sections. For the other joint sections 421b 421d, and 421e, driving control according to ordinary force control is executed. However, the driving control of the joint sections 421a, 421c and 421f and the driving control of the other joint sections 421b, 421d, and 421e differ only in whether to take or not to take a compensating torque $\tau_c$ into account when computing the torque command value τ described later, and the functional configuration of the joint sections 421a to 421f themselves may be similar. In other words, the joint sections 421a to 421f all include a functional configuration similar to the joint section 130 illustrated.

Also, in actuality, similarly to the configuration illustrated in FIG. 1, the microscope section 140 is attached to the front end of the arm section 110, but in FIG. 7, the state of the microscope section 140 being attached to the front end to the arm section 110 is expressed by schematically illustrating a link included in the arm section 110 between the joint section 130 and the microscope section 140.

(Joint Section)

The joint section 130 includes a joint driving section 131 and a joint state detection section 132 as functions thereof.

The joint driving section 131 is a driving mechanism for causing the joint section 130 to rotate. The joint driving section 131 may include the motor 424 and the motor driver 425 of the actuator 430 illustrated in FIG. 2.

The driving of the joint driving section 131 is controlled by a driving control section 260 of the control section 210 described later. Specifically, a value of torque (corresponding to the torque command value τ illustrated in FIG. 9 described later) that the joint section 130 needs to generate to put the microscope section 140 in a desired position and attitude according to an operation by the surgeon is computed by an ideal joint control section 250 of the control section 210 described later. The driving control section 260 provides a current command value corresponding to the computed torque command value τ to the joint driving section 131, and instructs the joint driving section 131 to drive the motor 424 in accordance with the current command value. By driving the motor 424 of the joint driving section 131 in accordance with the current command value, the joint section 130 is driven such that a torque corresponding to the torque command value τ is produced.

The joint state detection section 132 detects the state of the joint section 130. Herein, the state of the joint section 130 means the state of motion of the joint section 130. The state of the joint section 130 includes, for example, information such as the rotational angle, the rotational angular velocity, and the rotational angular acceleration of the joint section 130, as well as the torque acting on the joint section 130 (including the generated torque generated by the joint section 130 itself and an external torque acting on the joint section 130 from the outside), and the like. For example, in the case in which the surgeon attempts to move the microscope section 140 by a direct operation, the joint state detection section 132 detects the rotational angle and the external torque in the joint section 130 produced in association with the direct operation on the microscope section 140 by the surgeon.

Specifically, the joint state detection section 132 includes a rotational angle detection section 133 that detects the rotational angle of the joint section 130 and a torque detection section 134 that detects the torque acting on the joint section 130 as functions thereof. The rotational angle detection section 133 and the torque detection section 134 may include the encoder 427 and the torque sensor 428 of the actuator 430 illustrated in FIG. 2, respectively.

The joint state detection section 132 transmits information about the detected state of the joint section 130 to an arm state acquisition section 241 and a disturbance estimation section 251 of the control section 210 described later.

(Control Section)

The control section 210 may be included in the control apparatus 450 illustrated in FIG. 1. The control section 210 includes a whole body cooperative control section 240, an ideal joint control section 250, a driving control section 260, and a compensating torque computation section 270 as functions thereof. These functions are achieved by a processor included in the control section 210 executing computational processing in accordance with a predetermined program.

(Whole Body Cooperative Control)

The whole body cooperative control section 240 performs various mathematical operations related to whole body cooperative control. Herein, whole body cooperative control refers to control in a multi-link structure, in which a control value for each joint section required to cause the multi-link structure as a whole to perform a desired movement is computed, and each of the joint sections is made to move cooperatively with each other in accordance with the control value. Specifically, in the first embodiment, the whole body cooperative control section 240 computes a value of generated torque (control torque, corresponding to a generated torque $\tau_a$ illustrated in Formula (2) described later) which is the control value of each joint section 130 required for the arm section 110 and the microscope section 140 as a whole to perform a desired movement (for example, a movement corresponding to an operation performed by the surgeon). By having each joint section 130 operate in cooperation with each other in accordance with the control torque computed by the whole body cooperative control section 240, it becomes possible for the arm section 110 and the microscope section 140 as a whole to perform a desired movement.

Specifically, the whole body cooperative control section 240 includes an arm state acquisition section 241, an operation condition setting section 242, and a control torque computation section 243 as functions thereof.

The arm state acquisition section 241 acquires the state of the arm section 110 (arm state) on the basis of the state of the joint section 130 detected by the joint state detection section 132. Herein, the arm state means the state of motion of the arm section 110. For example, the arm state includes information about the position, velocity, acceleration, force, and the like of the arm section 110. By acquiring the arm state, the current position and the attitude of the arm section 110 and the microscope section 140, as well as the current force acting on the arm section 110, and the like may be gasped.

The control section 210 is provided with a storage section (not illustrated) that stores various information processed by the control section 210, and an internal model of the arm section 110 and the microscope section 140 is stored in the storage section. Herein, an internal model refers to a control model used in driving control of the observation apparatus 10, and includes information expressing the position and the attitude of the arm section 110 and the microscope section 140 to be controlled, as well as information about the motion of the arm section 110 and the microscope section 140. The arm state acquisition section 241 is able to acquire the current arm state by updating the internal model on the basis of the state of the joint section 130 detected by the joint state detection section 132.

The arm state acquisition section 241 provides information about the acquired arm state to the operation condition setting section 242 and the compensating torque computation section 270.

The operation condition setting section 242 sets an operation condition for calculating the control torque for driving control of the arm section 110 (that is, for driving control of the joint section 130). As the operation condition, for example, a constraint condition on calculating the control value or the like is set. For example, the constraint condition may be a limit on the rotational angle of each joint section 130 due to the geometric structure of the arm section 110, or a limit on the rotational angle, the rotational angular velocity and/or the rotational angular acceleration or the like of each joint section 130 set appropriately from the perspective of safety or the like.

The operation condition setting section 242 provides information about the arm state and information about the set operation condition to the control torque computation section 243.

The control torque computation section 243, under the operation condition set by the operation condition setting section 242, computes the control torque in each joint section 130 required to cause the microscope section 140 and the arm section 110 to perform a desired movement. In the control torque computation process by the control torque computation section 243, any of various publicly known techniques may be used. For example, in the first embodiment, the control torque computation section 243 computes the control torque by mathematical operations using generalized inverse dynamics. Note that, since the methods described in JP 2009-95959A, JP 2010-188471A, Patent Literature 1 (WO 2015/046081) cited above, and the like can be used as the method of computing the control torque using generalized inverse dynamics, a detailed description is omitted here.

The control torque computation section 243 provides information about the computed control torque to the ideal joint control section 250.

(Ideal Joint Control Section)

The ideal joint control section 250 performs various mathematical operations related to ideal joint control. Herein, ideal joint control refers to the driving control of each joint section 130 such that each joint section 130 produces an ideal response obeying a theoretical model.

Before describing a functional configuration of the ideal joint control section 250, ideal joint control will be described in detail. The motion of actuators (that is, the actuators 430 described above) provided in each joint section 130 of the arm section 110 is modeled by the equation of second-order lag motion expressed in Formula (1) below.

[Math. 1]

$$I_a \ddot{q}^{ref} = \tau_a + \tau_e - v_a \dot{q} \qquad (1)$$

Herein, q is the rotational angle of the actuator 430, $q^{ref}$ is a rotational angle target value of the actuator 430, $I_a$ is the inertial moment of the actuator 430, $\tau_a$ is the generated torque of the actuator 430, $\tau_e$ is the external torque acting on the actuator 430 from the outside, and $v_a$ is a viscous drag coefficient for the actuator 430. The above Formula (1) is a theoretical model expressing the motion of the actuator 430 in each of the joint sections 130.

Herein, as described above, a torque $\tau_a$ (generated torque $\tau_a$) to be generated by the actuators 430 of each joint section 130 in order to achieve the desired movement is computed by the control torque computation section 243. Therefore, ideally, by applying the generated torque $\tau_a$ computed for each actuator 430, a response obeying the theoretical model expressed in Formula (1) above should be realized in each actuator 430, or in other words, the desired operation should be realized in the arm section 110 and the microscope section 140.

However, in actuality, the influence of various disturbances causes error (modeling error) to occur between the actual motion in the actuator 430 and the theoretical model expressed in Formula (1) above in some cases. Modeling error may be divided roughly into error arising from mass properties, such as the mass, center of gravity, and inertia tensor of a multi-link structure (in other words, the arm section 110 and the microscope section 140 to be controlled), and error arising from factors such as friction and inertia internal to the actuator 430. Of these, the former modeling error arising from mass properties may be reduced comparatively easily during construction of the theoretical model by increasing the precision of computer-aided design (CAD) data and applying identification techniques.

On the other hand, the latter modeling error arising from factors such as friction and inertia internal to the actuator 430 is caused by phenomena which are difficult to model, such as friction in the reduction gear 426, for example. Accordingly, non-negligible modeling error may still remain during construction of the theoretical model expressing the motion of each actuator 430. Additionally, there is also a possibility of error occurring between the values of the inertia $I_a$ and the viscous drag coefficient $v_a$ in Formula (1) above, and these values in the actual actuator 430. These difficult-to-model errors arising from factors such as friction and inertia internal to the actuator 430 may become disturbances in the driving control of the actuator 430. Thus, because of the influence of such disturbances, in actuality, cases occur in which the motion of the actuator does not respond exactly like the theoretical model expressed in Formula (1) above, or in other words, the desired operation is not realized.

Accordingly, in the first embodiment, by adding an active control system to the actuators 430, the response of the actuators 430 is corrected by the ideal joint control section 250 such that an ideal response obeying the theoretical model expressed in Formula (1) above is produced. With this arrangement, since the actuators 430 produce an ideal response in which the influence of a disturbance is reduced, it becomes possible to control the rotational angle of the actuators 430 (that is, the rotational angle of each joint section 130) more precisely.

However, herein, in the first embodiment, for the joint sections 130 that function as torsion joint sections (namely, the joint sections 421a, 421c, and 421f), Formula (2) below, which incorporates a term that compensates the torque acting on the joint section 130 (that is, the actuator 430) due to the restoring force of the cable 495 described in (1-2. Disturbance caused by rigidity of cable) above, is treated as the theoretical model of the actuator 430. With this arrangement, the torque value (torque command value τ) computed by the ideal joint control section 250 becomes a torque value such that the actuator 430 produce an ideal response obeying the theoretical model illustrated in Formula (2) below, or in other words, a torque value that takes the restoring force of the cable 495 into account as a disturbance. Consequently, for these joint sections 421a, 421c, and 421f, it becomes possible to control the rotational angle of the actuators 430 (that is, the rotational angle of each of the joint sections 421a, 421c, and 421f) even more precisely. Note that regarding the driving control of the actuators 430 of the other joint sections 421b, 421d, and 421e, it is sufficient to treat Formula (1) above as the theoretical model.

[Math. 2]

$$I_a \ddot{q}^{ref} = \tau_a + \tau_c + \tau_e - v_a \dot{q} \qquad (2)$$

Herein, $\tau_c$ is the compensating torque, and is the torque value corresponding to the restoring force of the cable 495. Note that the specific value of the compensating torque $\tau_c$ may be computed by the compensating torque computation section 270. A specific method of computing the compensating torque $\tau_c$ by the compensating torque computation section 270 will be described later.

Figure 8:
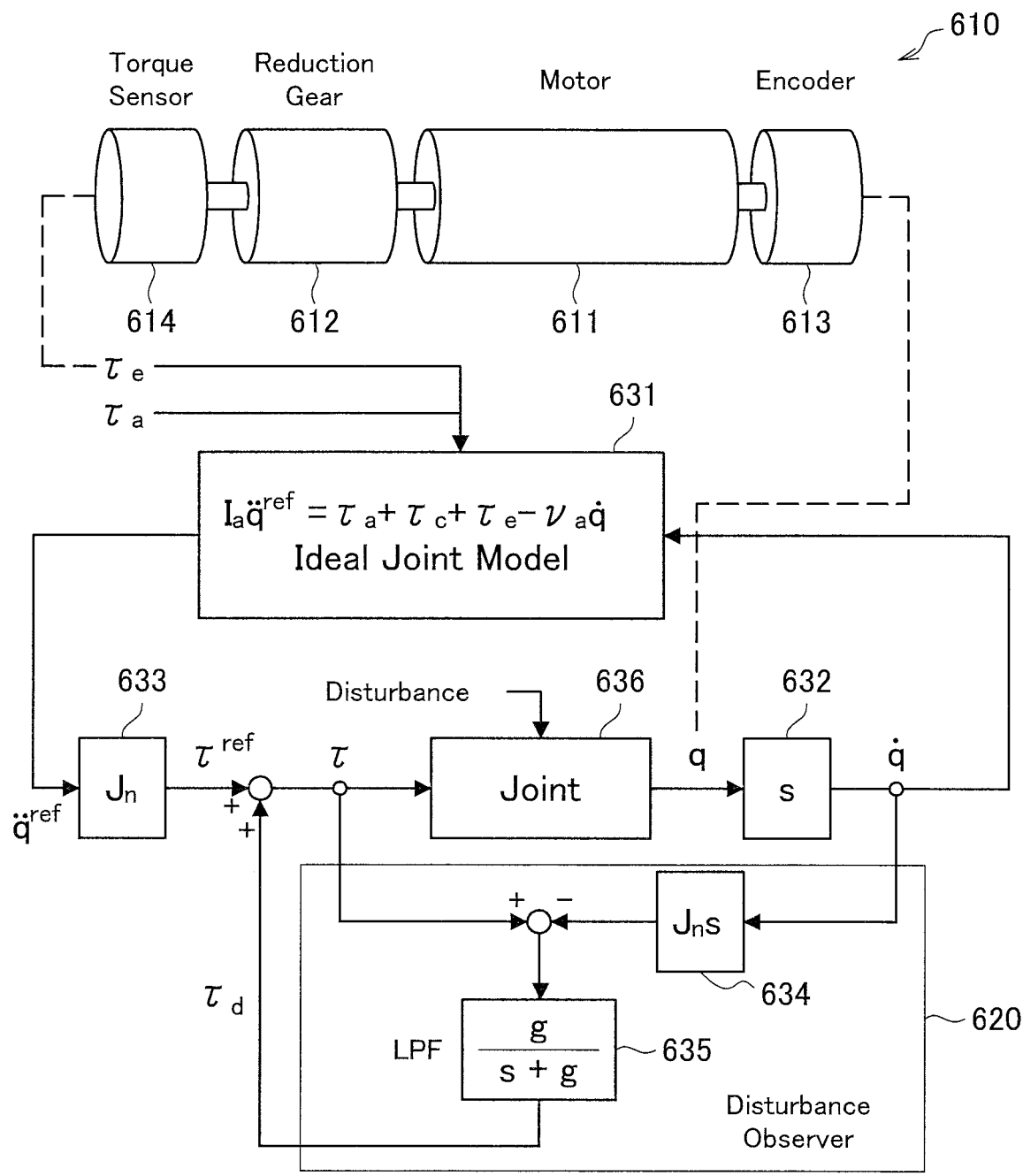
FIG. 8 is an explanatory diagram for explaining ideal joint control according to the first embodiment.

FIG. 8 will be referenced to describe ideal joint control in further detail. FIG. 8 is an explanatory diagram for explaining ideal joint control according to the first embodiment. In FIG. 8, abstract computing elements that perform various computations related to ideal joint control are illustrated schematically as blocks. Note that the block diagram illustrated in FIG. 8 is an illustration of a series of process for ideal joint control in the actuator 430 of any single joint section 130 corresponding to the joint sections 421a, 421c, and 421f that function as torsion joint sections from among the multiple joint sections 130 included in the arm section 110 of the observation apparatus 10. Note that with regard to the actuators 430 of the other joint sections 421b, 421d, and 421e, only the form of the theoretical model is different, and similar processes are executed.

Referring to FIG. 8, the actuator 610 illustrates a simulation of the functions of the actuator 430 illustrated in FIG. 2. In FIG. 8, a motor 611, a reduction gear 612, an encoder 613, and a torque sensor 614 are illustrated as component members of the actuator 610. These respectively correspond to the motor 424, the reduction gear 426, the encoder 427, and the torque sensor 428 illustrated in FIG. 2.

The computing element 631 is a computing element that perform computation in accordance with the ideal joint model of the actuator 610 (that is, joint sections 130)

expressed in Formula (2) above. The computing element 631 is able to take the generated torque $\tau_a$, the compensating torque $\tau_a$, the external torque $\tau_e$, and the rotational angular velocity (the first derivative of the rotational angle q) as input, and output the rotational angular acceleration target value (the second derivative of the rotational angle target value $q^{ref}$) expressed on the left side of Formula (2) above.

Herein, the actuator 610 producing a response obeying the ideal model expressed in Formula (2) above means nothing other than that when the right side of Formula (2) above is given, the rotational angular acceleration on the left side is achieved. However, as above, ideal response obeying Formula (2) above actually is not produced sometimes, due to the influence of disturbances. Accordingly, in the first embodiment, a disturbance observer 620 is introduced. A process is conducted in which a disturbance estimate value $\tau_d$, which is an estimate value of the torque arising from a disturbance by the disturbance observer 620, is computed, and the disturbance estimate value $\tau_d$ is used to correct the calculation result by the computing element 631.

Hereinafter, specific processes will be described in order. First, the generated torque $\tau_a$ for realizing a desired operation computed on the basis of a method used in typical force control (that is, the control torque computed by the control torque computation section 243), and the external torque $\tau_e$ detected by the torque sensor 614, are input into the computing element 631. Meanwhile, by inputting the rotational angle q of the actuator 610 detected by the encoder 613 into a computing element 632 that performs differential computations, the rotational angular velocity (the first derivative of the rotational angle q) of the actuator 610 is computed. By inputting the rotational angular velocity computed by the computing element 632, in addition to the generated torque $\tau_a$ and the external torque $\tau_e$ above, into the computing element 631, the rotational angular acceleration target value (the second derivative of $q^{ref}$) is computed by the computing element 631. The computed rotational angular acceleration target value is input into a computing element 633.

The computing element 633 is a computing element that computes the torque generated in the actuator 610, on the basis of the rotational angular acceleration of the actuator 610. In the first embodiment, specifically, the computing element 633 calculates a torque target value $\tau^{ref}$ by multiplying the rotational angular acceleration target value computed by the computing element 631 by the nominal inertia $J_n$ of the actuator 610. In ideal response, the actuator 610 is driven so as to output the torque target value $\tau^{ref}$, and thus the desired operation should be realized, but as described earlier, the influence of disturbances and the like is produced in the actual response in some cases. Consequently, in the first embodiment, the torque target value $\tau^{ref}$ is corrected using the disturbance estimate value $\tau_d$ computed by the disturbance observer 620.

The disturbance observer 620 computes the disturbance estimate value $\tau_d$, on the basis of the torque command value $\tau$ and the rotational angular velocity computed from the rotational angle q of the actuator 610 detected by the encoder 613. Herein the torque command value $\tau$ is the command value ultimately given to the actuator 610 after the influence of disturbances is corrected. In other words, in the control system illustrated in FIG. 8, the actuator 610 is driven so as to output the torque command value $\tau$. For example, in the case in which the disturbance estimate value $\tau_d$ is approximately zero, the torque command value $\tau$ becomes a value approximately equal to the torque target value $\tau^{ref}$.

Specifically, the disturbance observer 620 is made up of a computing element 634 and a computing element 635. The computing element 634 is a computing element that computes the torque generated in the actuator 610, on the basis of the rotational angular velocity of the actuator 610. Input into the computing element 634 is the rotational angular velocity computed by the computing element 632 on the basis of the rotational angle q detected by the encoder 613. The computing element 634 performs computations expressed by a transfer function $J_n s$ on the input rotational angular velocity, or in other words, finds the rotational angular acceleration by taking the derivative of the rotational angular velocity, and additionally multiplies the computed rotational angular acceleration by the nominal inertia $J_n$, and thereby computes an estimate value of the torque (torque estimate value) actually acting on the actuator 610.

Inside the disturbance observer 620, by taking the difference between the torque estimate value and the torque command value $\tau$, the value of the torque due to disturbances, that is, the disturbance estimate value $\tau_d$, is estimated. Specifically, the disturbance estimate value $\tau_d$ is the difference between the torque command value $\tau$ from the control in the previous step, and the torque estimate value from the control in the current step. Since the torque estimate value computed by the computing element 634 is based on an actual measured value, and the torque command value $\tau$ computed by the computing element 633 is based on an ideal theoretical model of the actuator 610 computed by the computing element 631, by taking the difference between the two, the influence of disturbances not taken into account by the theoretical model above can be estimated.

The computing element 635 is a computing element provided to prevent divergence of the system, and includes the function of a low-pass filter (LPF). The computing element 635 performs the computations expressed by the transfer function $g/(s+g)$ to thereby output only the low-frequency component with respect to an input value, and stabilize the system. The difference value between the torque estimate value and the torque target value $\tau^{ref}$ computed by the computing element 634 is input into the computing element 635, and the low-frequency component thereof is computed as the disturbance estimate value $\tau_d$.

After the disturbance estimate value $\tau_d$ is computed by the disturbance observer 620, the disturbance estimate value $\tau_d$ is added to the theoretical value, that is, the torque target value $\tau^{ref}$, to thereby compute the torque value to ultimately generate in the actuator 610, that is, the torque command value $\tau$. The computed torque command value $\tau$ is input into a block 636 representing a joint section. The block 636 expresses a simulation of the joint sections 130 (in other words, the actuator 610). In the block 636, the actuator 610 is driven on the basis of the torque command value $\tau$. Specifically, in the block 636, by converting the torque command value $\tau$ into a corresponding current value (current command value), and applying this current command value to the motor 611, the actuator 610 is driven so as to output torque corresponding to the torque command value $\tau$.

By executing the processes described above for each actuator 430 of the joint sections 130 that function as torsion joint sections (joint sections 421a, 421c, and 421f) among the joint sections 130 included in the arm section 110 of the observation apparatus 10, the driving of each of these actuators 430 is controlled to produce an ideal response obeying Formula (2) above. In addition, similarly, by executing the processes described above using Formula (1) above as the theoretical model for each actuator 430 of the other joint sections 421b, 421d, and 421e, the driving of each of these actuators 430 is controlled to produce an ideal response obeying Formula (1) above. With this arrangement, the desired movement is achieved by the arm section 110 and the microscope section 140 as a whole.

Note that for details regarding the ideal joint control described above, see JP 2009-269102, Patent Literature 1 (WO 2015/046081) cited above, and the like, for example.

Returning to FIG. 7, the description of the functional configuration of the ideal joint control section 250 continue. The ideal joint control section 250 executes the process of computing the torque command value τ from among the series of processes described with reference to FIG. 8. Specifically, the ideal joint control section 250 includes a disturbance estimation section 251 and a command value computation section 252 as functions thereof.

The disturbance estimation section 251 includes functions corresponding to the disturbance observer 620 illustrated in FIG. 8. The disturbance estimation section 251 computes the value of the torque due to the disturbance, namely a disturbance estimation value $\tau_d$, by taking the difference between the torque command value τ (the torque value that the joint section 130 should generate, which is computed in accordance with the theoretical model illustrated in Formula (2) above on the basis of the generated torque $\tau_a$ computed by the control torque computation section 243 and the external torque value acting on the joint section 130 detected by the rotational angle detection section 133), and the torque value acting on the joint section 130 computed on the basis of the rotational angle of the joint section 130 detected by the rotational angle detection section 133. The torque command value τ used by the disturbance estimation section 251 to compute the disturbance estimation value $\tau_d$ may be the torque command value τ in the control of the previous step.

The command value computation section 252 uses the disturbance estimation value $\tau_d$ computed by the disturbance estimation section 251 to compute the torque command value τ, which is a command value expressing the torque that is to be generated ultimately by the joint section 130 of the arm section 110. Specifically, the command value computation section 252 computes the torque command value τ by adding the disturbance estimation value $\tau_d$ computed by the disturbance estimation section 251 to the torque target value $\tau^{ref}$ computed from the theoretical model illustrated in Formula (2) above.

The command value computation section 252 provides information about the computed torque command value τ to the driving control section 260.

(Compensating Torque Computation Section)

The compensating torque computation section 270 computes the value of the compensating torque $\tau_c$ (the value of the compensating torque $\tau_c$ illustrated in Formula (2) above) to use when the ideal joint control section 250 computes the torque command value τ. In the first embodiment, the compensating torque computation section 270 computes, as the compensating torque $\tau_c$, a torque value corresponding to the restoring force of the cable 495 acting on the joint sections 421a, 421c, and 421f caused by the rotation of these joint sections 421a, 421c, and 421f that function as torsion joint sections from among the joint sections 130.

Specifically, as described in (1-2. Disturbance caused by rigidity of cable) above, the restoring force of the cable 495 occurs in association with the rotation of tin joint section 130, and thus may change depending on the rotational angle of the joint section 130. In other words, the compensating torque $\tau_c$ may be treated as a function of the rotational angle q ($\tau_c$=f(q)) of the joint section 130. For example, by prior experiment or the like, the relationship between the rotational angle q of the joint section 130 and the compensating torque $\tau_c$ is acquired and stored in a storage section provided in the control section 210 in a format such as a table or a graph. The compensating torque computation section 270 is able to reference the table, graph, or the like stored in the storage section, and on the basis of the information about the arm state provided from the arm state acquisition section 241, compute the value of the compensating torque corresponding to the current rotational angle of the joint section 130 to be controlled.

Figure 9:
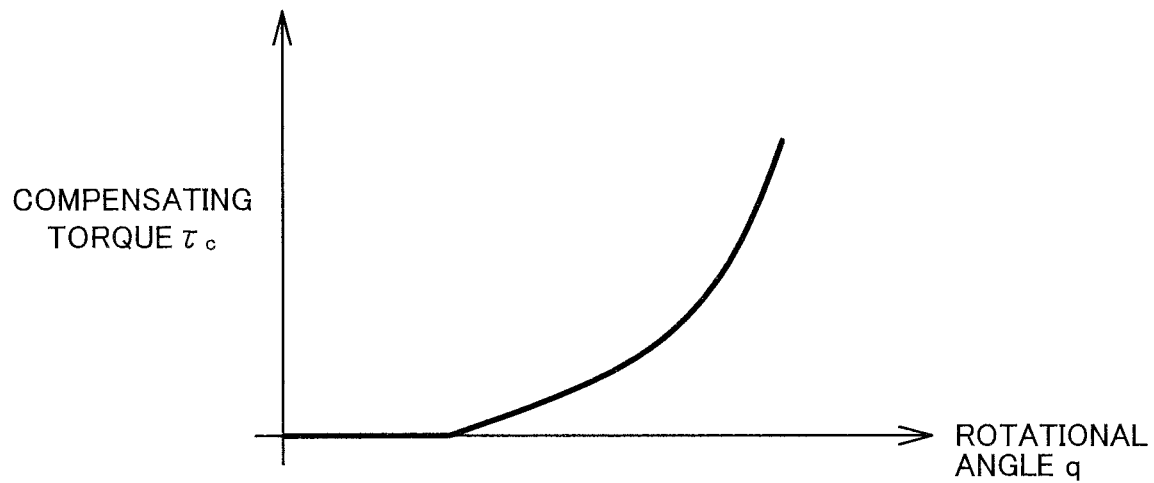
FIG. 9 is a graph illustrating an example of the relationship between a rotational angle q of a joint section and a compensating torque $\tau_c$.

As an example, FIG. 9 illustrates a graph illustrating the relationship between the rotational angle q of the joint section 130 and the compensating torque $\tau_c$. FIG. 9 is a graph illustrating an example of the relationship between the rotational angle q of the joint section 130 and the compensating torque $\tau_c$. It is sufficient to store a relationship as illustrated by such a graph in the above storage section. However, the first embodiment is not limited to such an example, and for example, the relationship between the rotational angle q of the joint section 130 and the compensating torque $\tau_c$ may also be acquired in advance by simulation, or computed by theoretical calculation.

The compensating torque computation section 270 provides information about the computed compensating torque $\tau_c$ to the command value computation section 252 of the ideal joint control section 250. In the command value computation section 252, as above, the torque command value τ is computed using the compensating torque $\tau_c$.

(Driving Control Section)

On the basis of the torque command value τ computed by the command value computation section 252, the driving control section 260 controls the driving of the joint driving section 131 of the joint section 130 such that a torque corresponding to the torque command value τ is generated in the joint section 130. Specifically, the driving control section 260 is able to convert the torque command value τ into a corresponding current command value, and instruct the motor driver 425 included in the joint driving section 131 to drive the motor 424 included in the joint driving section 131 by the current corresponding to the current command value.

According to the control from the driving control section 260, each joint section 130 included in the arm section 110 is driven such that a torque corresponding to the torque command value τ computed by the ideal joint control section 250 is generated, and therefore the arm section 110 is driven such that a desired movement is achieved.

The above references FIG. 7 to describe a functional configuration of the observation apparatus 10 according to the first embodiment. As described above, according to the first embodiment, when computing the torque command value τ for controlling the driving of the joint sections 130 that function as torsion joint sections (namely, the joint sections 421a, 421c, and 421f), the torque command value τ is computed by taking into account the restoring force of the cable 495. With this arrangement, the value of the external torque imparted to the arm section 110 when operated by the surgeon becomes a value in which the influence due to the restoring force of the cable 495 has been canceled out, making it possible for the surgeon to operate the arm section 110 without feeling a sense of resistance due to the restoring force of the cable 495. In other words, it becomes possible to obtain a smooth operational feeling, regardless of the rotational angle of the joint sections 130. Thus, operability for the surgeon can be improved. With this arrangement, it becomes possible to reduce the burden on the surgeon while also performing surgery more smoothly, and an advantageous effect of improving the safety of surgery can also be obtained.

Herein, in the observation apparatus 10 provided with the electronic imaging microscope section 140 like in the first embodiment, in the case of capturing the surgical site at a high magnification, slight movements of the microscope section 140 lead to large movements of the field of view. In contrast, according to the first embodiment, since operability for the surgeon can be improved as above, it becomes possible to position the microscope section 140 more easily. In this way, by applying the technology according to the first embodiment to the observation apparatus 10 provided with the electronic imaging microscope section 140 in particular, it becomes possible to obtain an even greater advantageous effect of reducing the burden on the surgeon and making surgery proceed more smoothly.

Note that the functional configuration illustrated in FIG. 7 is merely one example of the functional configuration of the observation apparatus 10, and the functional configuration of the observation apparatus 10 is not limited to such an example. It is sufficient for the observation apparatus 10 to be capable of achieving the functions described above as a whole, and the functional configuration thereof is arbitrary. For example, the functions provided in the control section 210 of the observation apparatus 10 do not all have to be executed in a single apparatus, and may also be executed by the cooperation of multiple apparatus.

Additionally, it is possible to develop a computer program for realizing each function of the control section 210 of the observation apparatus 10 illustrated in FIG. 7, and implement the computer program in a processing apparatus such as a PC. In addition, a computer-readable recording medium storing such a computer program may also be provided. The recording medium may be a magnetic disk, an optical disc, a magneto-optical disc, flash memory, or the like, for example. Additionally, the above computer program may also be delivered via a network, for example, without using a recording medium.

1-4. Driving Control Method

FIG. 10 will be referenced to describe a processing procedure of the driving control method of the observation apparatus 10 according to the first embodiment. FIG. 10 is a flowchart illustrating an example of the processing procedure of the driving control method of the observation apparatus 10 according to the first embodiment. Note that in FIG. 10, from among the driving control method of the observation apparatus 10 according to the first embodiment, the processing procedure of the driving control method when controlling the driving of the joint sections 421a, 421c, and 421f that function as torsion joint sections is illustrated. In the driving control method of the other joint sections 421b, 421d, and 421e, the process in step S107 described later may not be executed, and in step S109, a torque command value that does not take the compensating torque into account may be computed.

Herein, each process illustrated in FIG. 10 corresponds to a process executed by the control section 210 of the observation apparatus 10 illustrated in FIG. 7. Since the details of each of these processes already have been described when describing the functional configuration of the observation apparatus 10, in the following description of the processing procedure of the driving control method, a detailed description of each process will be omitted.

Referring to FIG. 10, in the driving control method according to the first embodiment, first, the arm state is acquired on the basis of the states of the joint sections 130 (step S101). The process illustrated in step S101 corresponds to the process executed by the arm state acquisition section 241 illustrated in FIG. 7.

Next, an operation condition for computing the control torque (generated torque $\tau_a$) of each joint section 130 by mathematical operations related to whole body cooperative control is set (step S103). The process illustrated in step S103 corresponds to the process executed by the operation condition setting section 242 illustrated in FIG. 7.

Next, on the basis of the an state and the operation condition, mathematical operations for whole body cooperative control are performed, and the generated torque $\tau_a$ in the joint sections 130 is computed (step S105). The process illustrated in step S105 corresponds to the process executed by the control torque computation section 243 illustrated in FIG. 7.

Next, the compensating torque $\tau_c$ is computed (step S107). In step S107, a torque value corresponding to the restoring force of the cable 495 is computed as the compensating torque $\tau_c$. The process illustrated in step S107 corresponds to the process executed by the compensating torque computation section 270 illustrated in FIG. 7.

Next, mathematical operations for ideal joint control taking the compensating torque into account are performed, and the torque command value $\tau$ is computed from the generated torque $\tau_a$ (step S109). The process illustrated in step S109 corresponds to the process executed by the ideal joint control section 250 illustrated in FIG. 7.

Next, on the basis of the computed torque command value $\tau$, the driving of the joint sections 130 of the arm section 110 is controlled (step S111). The process illustrated in step S111 corresponds to the process executed by the driving control section 260 illustrated in FIG. 7.

The above references FIG. 10 to describe the processing procedure of the driving control method of the observation apparatus 10 according to the first embodiment.

1-5. Modifications

In the description of the first embodiment above, the value of the compensating torque $\tau_c$ is acquired manually by prior experiment or the like, for example, and is stored in a storage section provided in the observation apparatus 10. However, the first embodiment is not limited to such an example, and the value of the compensating torque $\tau_c$ may also be acquired automatically by the observation apparatus 10 and stored in the above storage section. In other words, the compensating torque computation section 270 of the observation apparatus 10 may be provided with a function of automatically updating the value of the compensating torque $\tau_c$.

Specifically, in the observation apparatus 10, as described above, besides the case of causing the arm section 110 to move due to a direct operation by the surgeon, control to drive the actuators 430 and cause the arm section 110 to move may be performed by following operating input from the surgeon via an input apparatus such as a footswitch, or an instruction from a navigation apparatus, for example. When causing the arm section 110 to move automatically in this way, no external force other than gravity is operating on the microscope section 140 and the arm section 110. Consequently, in the case in which a movement causing certain joint sections 130 that function as torsion joint sections to rotate is performed while the arm section 110 is being moved automatically, it becomes possible to detect the restoring force of the cable 495 occurring in association with the rotation with the torque detection section 134 (that is, the torque sensor 428 of the actuator 430) of each joint section 130.

Accordingly, in the first embodiment, when the arm section 110 is moved automatically, preferably, the restoring force of the cable 495 is detected, and on the basis of the value, the compensating torque computation section 270 continually updates the value of the compensating torque $\tau_c$ stored in the storage section. For example, since the rigidity of the cable 495 may change due to deterioration over time or the like, the relationship between the rotational angle of the joint section 130 and the compensating torque $\tau_c$ may also change. By updating the value of the compensating torque $\tau_c$ automatically as above, changes in the relationship between the rotational angle of the joint section 130 and the compensating torque $\tau_c$ due to such aging can be accommodated, making it possible to compute the torque command value $\tau$ using a more accurate value of compensating torque $\tau_c$.

2. Second Embodiment

2-1. Background Underlying Second Embodiment

Before describing the second embodiment of the present disclosure in detail, the background leading up to the inventors' conceiving of the second embodiment will be described.

Typically, a joint section of an arm section of an observation apparatus, like the one illustrated in FIG. 1 for example, includes a bearing, and is configured to be capable of rotating smoothly. With this arrangement, when the surgeon operates the microscope section directly, light operability may be achieved.

Herein, for example, in an observation apparatus provided with an electronic imaging microscope section on the front end of an arm section, the microscope section may be configured relatively more compact and lightweight compared to an optical microscope section in which the surgeon performs magnified observation of a surgical site peering in directly from an eyepiece. This is because in an electronic imaging microscope section, since it is not necessary to provide an eyepiece lens, and furthermore since the magnification can be adjusted by using not only an optical zoom function but also an electronic zoom function, the optical system installed in the microscope section can be simplified. When the microscope section is configured in a compact and lightweight manner in this way, since the inertia becomes smaller, the surgeon becomes able to move the microscope section with less force. In other words, in an observation apparatus provided with an electronic imaging microscope section, the operational feeling for the surgeon becomes significantly lighter.

However, if the microscope section moves due to even a tiny force, there is a risk that the microscope section will move more than expected, and on the contrary impair operability for the surgeon. In particular, in an observation apparatus provided with an electronic imaging microscope section, a surgical site is captured at a high magnification in some cases. In the case of performing image capture at such a high magnification, since slight movements of the microscope section lead to large movements of the field of view, when the surgeon moves the microscope section to a position where a desired image is obtained, positioning the microscope section becomes difficult.

Accordingly, up until now, typically, in an observation apparatus provided with an electronic imaging microscope section, a mechanical friction load is applied to each joint section, particularly the joint sections corresponding to the first axis $O_1$ to the third axis $O_3$ involved in control of the attitude of the microscope section, thereby causing the microscope section not to move unless a relatively large force is imparted. This mechanical friction load may be achieved by a mechanism that uses a spring such as a wave washer to press a friction plate or the like against the surface of another friction plate that rotates together with the joint section.

However, when the arm section is made to move automatically not by a direct operation by the surgeon, but by an actuator, for example, such a mechanical friction load becomes energy loss from the perspective of the output of the actuator, leading to increased power consumption. Also, since the motor and the reduction gear of the actuator must be designed to account for existence of the mechanical friction load, the motor and the reduction gear become bulkier in proportion with the friction load, and as a result, there is a risk of creating increases in the number of parts and increases in manufacturing costs. Furthermore, when the mechanism that applies the friction load mechanically is applied, vibration of the microscope section due to the stick-slip phenomenon occurs, making it difficult to observe a surgical site safely, and there is also a risk of impeding the smooth execution of surgery.

In light of the above circumstances, the inventors investigated technologies capable of improving the operability of the observation apparatus without applying a friction load to each joint section mechanically, and as a result, conceived the second embodiment of the present disclosure. Hereinafter, the second embodiment will be described in detail.

2-2. Details of Second Embodiment

The configuration of the observation system and the observation apparatus according to the second embodiment is similar to the configuration of the observation system 1 and the observation apparatus 10 according to the first embodiment illustrated in FIG. 1. Consequently, a description thereof is omitted here.

Also, the functional configuration of the observation apparatus according to the second embodiment is substantially similar to the functional configuration of the observation apparatus 10 according to the first embodiment illustrated in FIG. 7. However, in the second embodiment, in the functional configuration of the observation apparatus 10 illustrated in FIG. 7, the functions of the ideal joint control section 250 and the compensating torque computation section 270 are different from the first embodiment. Specifically, in the second embodiment, the ideal joint control section 250 computes the torque command value $\tau$ using Formula (3) below instead of Formula (2) above as the theoretical model of the response in each joint section 130.

[Math. 3]

$$I_a \ddot{q}^{ref} = \tau_a + \tau_e - v_a \dot{q} + \tau_c' = \tau_a + \tau_e - v_a \dot{q} - c \times \mathrm{sgn}(dq) \qquad (3)$$

Herein, $\tau_c'$ is a term expressing the compensating torque similarly to the first embodiment, but in the second embodiment, unlike the first embodiment, $\tau_c'$ is a torque value corresponding to a friction load which may be applied to each joint section 130. Specifically, as illustrated in Formula (3) above, $\tau_c' = -c \times \mathrm{sgn}(dq)$ is used as $\tau_c'$. Herein, c is a constant, and dq is the rite of change in the rotational angle of the joint section 130, or in other words, the rotation speed. In other words, $\tau_c'$ expresses a torque value of fixed magnitude whose direction changes depending on the sign of the rotation speed of the joint section 130. Since only the form of the theoretical model used is different, and specific computational process performed by the ideal joint control section 250 is similar to the first embodiment, a detailed description is omitted here. With this arrangement, in the second embodiment the torque command value τ is computed while taking the friction load into account.

However, in the second embodiment, the joint sections 130 for which the ideal joint control section 250 computes the torque command value τ using Formula (3) above may be the joint sections 130 corresponding to the first axis $O_1$ to the third axis $O_3$ involved in control of the attitude of the microscope section 140 (in other words, in the case of the exemplary configuration of the observation apparatus 10 illustrated in FIG. 1, the joint sections 421*a* to 421*c*). This is because rotation in these joint sections 421*a* to 421*c* is thought to particularly influence the operational feeling for the surgeon. In this case, regarding the other joint sections 421*d* to 421*f*, it is sufficient for the ideal joint control section 250 to compute the torque command value using Formula (1) above as the theoretical model.

However, the second embodiment is not limited to such an example, and the joint sections to which Formula (3) above is applied (in other words, for which the torque command value τ accounting for the friction load is computed) among the joint sections 421*a* to 421*f* included in the arm section 420 of the observation apparatus 10 may be arbitrary. For example, the torque command value τ may be computed using Formula (3) above for all of the joint sections 421*a* to 421*f*. In the second embodiment, if Formula (3) above is applied to the driving control of the joint sections that may exert a relatively large influence on the operational feeling for the surgeon from among the joint sections 421*a* to 421*f* the advantageous effect thereof is obtainable.

The compensating torque computation section 270 computes the specific value of the above compensating torque $\tau_c'$ on the basis of the current arm state. Note that the specific value of the constant c is acquired by performing prior experiment, simulation, or the like, for example, and is stored in a storage section provided in the observation apparatus 10 as a value by which a friction load of a desired magnitude that improves operability for the surgeon occurs in the joint sections 130, in consideration of the mechanical configuration and the like of the arm section 110 and the joint sections 130. The compensating torque computation section 270 is able to compute the specific value of the above compensating torque $\tau_c'$ on the basis of the current arm state provided from the arm state acquisition section 241 and the value of the constant c obtained by referencing the storage section. The compensating torque computation section 270 provides information about the computed compensating torque $\tau_c'$ to the ideal joint control section 250. The ideal joint control section 250 executes a series of calculation processes using the provided value of the compensating torque $\tau_c'$, and computes the torque command value τ.

The above describes the second embodiment. As described above, according to the second embodiment, instead of applying a friction load mechanically to each joint section 130, when calculating the torque command value τ with respect to the joint sections 130, by introducing a compensating torque $\tau_c'$ term corresponding to a friction load, the torque command value τ that takes the friction load into account is computed. Consequently, even without providing a mechanism that applies a friction load mechanically, it becomes possible to impart a predetermined sense of resistance to an operation by the surgeon. Thus, operability for the surgeon can be improved without causing a situation to occur in which the operational feeling is so light that it actually lowers operability for the surgeon.

Herein, for example, in the case of applying a friction load mechanically to each joint section like a typical observation apparatus, as described above, the friction load is inevitably applied even when causing the arm section to move automatically by actuators, thereby creating several problems such as increased power consumption, bulkier actuators, an increased number of parts, and vibration of the microscope section due to the stick-slip phenomenon. On the other hand, according to the second embodiment, since a friction load is applied virtually by calculation, when causing the arm section 110 to move automatically, for example, driving control of each joint section 130 can be performed using the normal formula (for example, Formula (1) above) without including the compensating torque $\tau_c'$ term. In this way, in the case in which it is not necessary to apply a friction load on purpose in consideration of operability for the surgeon, driving control of each joint section 130 can be performed without applying the friction load, thereby making it possible to solve problems like the above.

Note that since the processing procedure of the driving control method of the observation apparatus 10 according to the second embodiment is substantially similar to the processing procedure of the driving control method according to the first embodiment illustrated in FIG. 10, a detailed description is omitted. However, in the second embodiment, in step S107 illustrated in FIG. 10, the compensating torque $\tau_c'$ corresponding to the friction load described above may be computed as the compensating torque, and in step S109, the torque command value τ may be computed using the compensating torque $\tau_c'$.

2-3. Modifications

2-3-1. Magnitude of Compensating Torque $\tau_c'$

In the above description of the second embodiment, although the compensating torque $\tau_c'$ corresponding to the friction load changes sign, the magnitude is constant. However, the second embodiment is not limited to such an example, and the magnitude of the compensating torque $\tau_c'$ may also be changed appropriately according to a predetermined condition. In other words, the compensating torque computation section 270 of the observation apparatus 10 may also be provided with a function of computing a compensating torque $\tau_c'$ of different magnitude depending on a predetermined condition.

Specifically, for example, the compensating torque computation section 270 may change the magnitude of the compensating torque $\tau_c'$ corresponding to the friction load according to the zoom magnification of the microscope section 140. As described above, in the case of a high zoom magnification, slight movements of the microscope section 140 lead to large movements of the field of view. Consequently, for example, the compensating torque computation section 270 increases the value of the compensating torque $\tau_c'$ in the case in which the zoom magnification of the microscope section 140 is high, and decreases the value of the compensating torque $\tau_c'$ in the case in which the zoom magnification of the microscope section 140 is low. With this arrangement, since a larger sense of resistance is imparted to an operation by the surgeon in the case in which the zoom magnification is high, unintended movement of the microscope section 140 (that is, movement of the field of view) can be suppressed, and operability for the surgeon can be raised further.

Alternatively, for example, the compensating torque computation section 270 may change the magnitude of the compensating torque $\tau_c'$ corresponding to the friction load according to the rotational angle of the joint sections 130. For example, the compensating torque computation section 270 increases the value of the compensating torque $\tau_c'$ as the rotational angle of the joint sections 130 approaches the limit of the movable range (for example, the mechanical movable range). With this arrangement, because of the increased sense of resistance, the surgeon becomes able to grasp that the rotational angle of the joint sections 130 is approaching the limit of the movable range. If the surgeon attempts to rotate a joint section 130 without realizing that the rotational angle of the joint section 130 is approaching the limit of the movable range, the joint section 130 will stop rotating suddenly, and thus there is a risk that operability for the surgeon will be reduced. Also, since the rotation of the joint section 130 is stopped mechanically, there is also a risk of imposing a mechanical load on the observation apparatus 10. In contrast, since by changing the magnitude of the compensating torque $\tau_c'$ depending on the rotational angle of the joint sections 130 as above, the surgeon is able to grasp intuitively that the rotational angle of the joint sections 130 is approaching the limit of motion, an improvement in operability for the surgeon and an improvement in safety may be achieved.

2-3-2. Combination of First and Second Embodiments

In the first embodiment, a torque value corresponding to the restoring force of the cable 495 is used as the compensating torque $\tau_c$. Also, in the second embodiment, a torque value corresponding to a friction load is used as the compensating torque $\tau_c'$. Herein, in the rotation of the joint sections 130, cases may also exist in which it is desirable to apply a friction load to a joint section 130 that functions as a torsion joint section on which the restoring force of the cable 495 may act. Consequently, during driving control of the joint sections 130, the first embodiment may be combined with the second embodiment. Specifically, the driving of the joint sections 130 may be controlled using a theoretical model that additionally introduces the compensating torque $\tau_c$ related to the restoring force of the cable 495 into Formula (3) above. In this case, the ideal joint control section 250 illustrated in FIG. 7 computes the torque command value $\tau$ by using Formula (4) below instead of Formula (3) above as the theoretical model of the response in the joint sections 130 to be controlled.

[Math. 4]

$$I_a \ddot{q}^{ref} = \tau_a + \tau_c + \tau_e - \nu_a \dot{q} + \tau_c' = \tau_1 + \tau_c + \tau_e - \nu_a \dot{q} - c \times \text{sgn}(\dot{q}) \quad (4)$$

According to this configuration, a torque command value $\tau$ that takes into account both the influence due to the restoring force of the cable 495 and the influence due to the friction load can be computed. Consequently, since the advantageous effects obtained by both the first and second embodiments can be obtained, operability for the surgeon can be improved even further.

3. Summary of First and Second Embodiments

Both of the first and second embodiments described above improve operability for the surgeon by introducing a compensating torque term into a theoretical model that expresses the response of the joint sections 130. Specifically, the first embodiment introduces the compensating torque $\tau_c$ that cancels out the influence due to the restoring force of the cable 495 on an operation by the surgeon. Also, the second embodiment introduces the compensating torque $\tau_c'$ by which a friction load is applied to an operation by the surgeon. Since the restoring force of the cable 495 and the friction load both can be treated as disturbances in the calculation of the torque command value $\tau$, when computing the torque command value $\tau$, the first and second embodiments may be considered to be introducing the compensating torques $\tau_c$ and $\tau_c'$, whereby the influence of a disturbance referred to as the restoring force of the cable 495 is canceled out, and the influence of a disturbance referred to as the friction load is applied, with respect to an operation by the surgeon.

Herein, from the perspective of operability for the surgeon, an operational feeling that is too heavy (in other words, the arm section 110 and the microscope section 140 do not move much even though a large force is being applied) poses a problem, and an operational feeling that is too light (in other words, the arm section 110 and the microscope section 140 move too much even though only a small force is being applied) poses a problem. In other words, to provide favorable operability to the surgeon, when the surgeon attempts to move the arm section 110 and the microscope section 140 by a direct operation, it is considered important to keep the torque that the surgeon imparts to each joint section 130 of the arm section 110 (that is, the external torque acting on the joint sections 130 during an operation) contained in a fixed range that is not too large and not too small, whereby a favorable operational feeling for the surgeon may be achieved.

In that sense, both the first and second embodiments described above are considered to adjust the torque that the surgeon imparts to each joint section 130 of the arm section 110 during an operation by introducing the compensating torque $\tau_c$ and $\tau_c'$ terms for compensating the influence of a disturbance (the restoring force of the cable 495, or the friction load) into the theoretical model that expresses the response of the joint sections 130, such that the torque is contained within a fixed range, and operability is improved for the surgeon. Note that, if stated differently, the fixed range for the torque may be set appropriately such that the surgeon obtains a comfortable operational feeling in consideration of the situation in which the surgeon operates the arm section 110 and the microscope section 140. The fixed range may be set in advance by the surgeon (user) or a designer or the like of the observation system 1, for example. Alternatively, like the modification described in (2-3-1. Magnitude of compensating torque $\tau_c'$) above, for example, in the case in which the magnitude of the compensating torque $\tau_c'$ is changed appropriately according to a predetermined condition, the fixed range may be changed dynamically during an operation by the user according to a condition such as the zoom magnification.

On the other hand, in the observation apparatus 10, many factors that act as disturbances on the driving control of each joint section 130 may exist besides the restoring force of the cable 495 and the friction load. Among the disturbances caused by these other factors, for disturbances whose influence on the joint sections 130 (that is, the torque acting on the joint sections 130 due to the disturbance) is estimable in a situation in which the disturbance may occur or in a case in which the disturbance has occurred, similarly to the first and second embodiments, by introducing a compensating torque corresponding to the disturbance, it is possible to adjust the torque that the surgeon imparts to each joint section 130 of the arm section 110 during an operation, such that the torque is contained within the fixed range, and operability is improved for the surgeon. In other words, the present disclosure is not limited to the first and second embodiments, and the torque command value τ may also be computed using a formula in which terms for compensating torques corresponding to other disturbances have been added to a theoretical model of the response in each joint section 130. Even in this case, by appropriately setting the values of the compensating torques corresponding to other disturbances, the torque that the surgeon imparts to each joint section 130 of the arm section 110 during an operation may be adjusted appropriately to be contained within a fixed range while taking the influence of the other disturbances into account, thereby making it possible to improve operability for the surgeon.

Examples of such other disturbances include the resistance to rotation in the joint sections 130 caused by the processing precision and the assembly precision. For example, the joint sections 130 may be configured such that a shaft is rotatably supported by a hearing, but because of tiny deformations in the outer diameter of the shaft and the inner diameter of the bearing or the like, there is a possibility that the smoothness of rotation in the joint sections 130 is not necessarily uniform depending on the rotational angle. In such a case, it is sufficient to acquire in advance the relationship between the rotational angle of the joint sections 130 and the resistance to rotation in the joint sections 130, and when actually controlling the driving of the joint sections 130, introduce a compensating torque term corresponding to this resistance to rotation into the theoretical model on the basis of the relationship. With this arrangement, it becomes possible to drive the joint sections 130 to cancel out the resistance to rotation with respect to an operation by the surgeon.

Note that since the resistance to rotation in the joint sections 130 given as an example herein is caused by the processing precision and the assembly precision as above, if control that takes the influence due to this disturbance into account is actually attempted, it is necessary to perform the work of acquiring the relationship between the rotational angle of the joint sections 130 and the resistance to rotation in the joint sections 130 for every observation apparatus 10. However, combining the above with the function of updating the relationship automatically described in (1-5. Modifications) above is convenient, because it becomes no longer necessary to perform the work of acquiring the relationship manually.

4. Supplement

The preferred embodiments of the present disclosure have been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

For example, the foregoing describes an embodiment in which the support arm apparatus is an observation apparatus in which an electronic imaging microscope section is provided on the front end of an arm section thereof, but the present disclosure is not limited to such an example. The technology according to the present disclosure preferably is applied to all types of support arm apparatus, regardless of the type of medical tool supported on the front end of the arms section. As described above, since the technology according to the present disclosure makes it possible to improve operability for a user when the user performs an operation that causes the arm section of the support arm apparatus to move, as long as the user performs an operation causing an arm section to move, similar advantageous effects can be exhibited by applying the technology according to the present disclosure, regardless of the type of support arm apparatus.

For example, the technology according to the present disclosure may also be applied to a support gum apparatus (endoscopic apparatus) that supports an endoscope by an arm section. In this case, for example, a mode is anticipated in which a scopist performs operations such as inserting and drawing out a lens tube of the endoscope with respect to a patient by moving an arm section that supports the endoscope while touching the arm section directly. By applying the technology according to the present disclosure to the driving control of the arm section of such an endoscopic apparatus, the torque that the scopist imparts to each joint section of the arm section during an operation is adjusted appropriately to be contained within a fixed range while taking the influence of disturbances into account, thereby making it possible to improve operability when moving the arm section by the scopist (that is, operability when moving the endoscope).

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1)

A medical observation apparatus including:

an imaging section that captures an observation target to perform magnified observation of the observation target;

an arm section that supports the imaging section and includes multiple links joined to each other by joint sections; and a driving control section that, by controlling a generated torque in at least one joint section to be controlled from among the multiple joint sections, controls a driving of the at least one joint section, in which the driving control section controls the driving of the at least one joint section such that an external torque acting on the at least one joint section according to an operation on the arm section is contained in a fixed range.

(2)

The medical observation apparatus according to (1), in which the driving control section controls the driving of the at least one joint section such that the external torque is contained in a fixed range by compensating an influence of a disturbance caused by a rigidity of a cable extending inside the at least one joint section to control the generated torque in the joint sections.

(3)

The medical observation apparatus according to (2), in which the disturbance caused by the rigidity of the cable is a torque imparted to the at least one joint section by a restoring force that occurs because the cable is twisted m association with a rotation of the at least one joint section.

(4)

The medical observation apparatus according to any one of (1) to (3), in which the driving control section controls the driving of the at least one joint section such that the external torque is contained in a fixed range by compensating a torque acting as a resistance to the external torque to control the generated torque in the joint sections.

(5)

The medical observation apparatus according to (4), in which the torque acting as a resistance to the external torque is a torque of fixed magnitude whose direction depends on a rotation speed of the at least one joint section.

(6)

The medical observation apparatus according to (4), in which a magnitude of the torque acting as a resistance to the external torque increases as a rotational angle of the at least one joint section approaches a limit of a movable range.

(7)

The medical observation apparatus according to (4), in which a magnitude of the torque acting as a resistance to the external torque changes according to a zoom magnification when the imaging section captures the observation target.

(8)

A driving control method including:

controlling, by a processor, a driving of at least one joint section to be controlled by controlling a generated torque in the at least one joint section from among multiple joint sections in an arm section that supports an imaging section that captures an observation target to pert nu magnified observation of the observation target, the arm section including multiple links joined to each other by the joint sections, in which the driving of the at least one joint section is controlled such that an external torque acting on the at least one joint section according to an operation on the arm section is contained in a fixed range.

(9)

A medical observation system including:

a medical observation apparatus that captures an observation target; and a display apparatus that displays an image of the observation target captured by the medical observation apparatus, in which the medical observation apparatus includes an imaging section that captures an observation target to perform magnified observation of the observation target, an arm section that supports the imaging section and includes multiple links joined to each other by joint sections, and a driving control section that, by controlling a generated torque in at least one joint section to be controlled from among the multiple joint sections, controls a driving of the at least one joint section, and the driving control section controls the driving of the at least one joint section such that an external torque acting on the at least one joint section according to an operation on the arm section is contained in a fixed range.

(10)

A support arm apparatus including:

an arm section including multiple links joined to each other by joint sections; and a driving control section that, by controlling a generated torque in at least one joint section to be controlled from among the multiple joint sections, controls a driving of the at least one joint section, in which the driving control section controls the driving of the at least one joint section such that an external torque acting on the at least one joint section according to an operation on the arm section is contained in a fixed range.

REFERENCE SIGNS LIST 1 observation system
10 observation apparatus
110, 420 arm section
130, 421a to 421f joint section
131 joint driving section
132 joint state detection section
133 rotational angle detection section
134 torque detection section
140, 440 microscope section
210 control section
240 whole body cooperative control section
241 arm state acquisition section
242 operation condition setting section
243 control torque computation section
250 ideal joint control section
251 disturbance estimation section
252 command value computation section
260 driving control section
270 compensating torque computation section
410 base section
422a to 422d link
430 actuator
424, 611 motor
425 motor driver
426, 612 reduction gear
427, 613 encoder
428, 614 torque sensor
450 control apparatus

The invention claimed is:

1. A medical observation apparatus comprising:
an imaging device that captures a magnified image of an observation target;
an arm that supports the imaging device and includes multiple links joined to each other by multiple joints; and
circuitry configured to:
determine a control torque for at least one joint to be controlled from among the multiple joints;
determine a torque command value based on the control torque and an external torque, wherein the torque command value increases as magnification of the observation target increases; and
control driving of the at least one joint based on the torque command value such that the external torque acting on the at least one joint according to an operation on the arm is within a fixed range.

2. The medical observation apparatus according to claim 1, wherein
the circuitry is configured to maintain the external torque within the fixed range by compensating an influence of a disturbance caused by a rigidity of a cable extending inside the at least one joint to control the control torque in the joints.

3. The medical observation apparatus according to claim 2, wherein the disturbance caused by the rigidity of the cable is a torque imparted to the at least one joint by a restoring force that occurs when the cable is twisted in association with a rotation of the at least one joint.

4. The medical observation apparatus according to claim 1, wherein
the circuitry is configured to control driving of the at least one joint such that the external torque is within the fixed range by compensating a torque acting as a resistance to the external torque to control the control torque in the at least one joint.

5. The medical observation apparatus according to claim 4, wherein
the torque acting as a resistance to the external torque is a torque of fixed magnitude whose direction depends on a rotation speed of the at least one joint.

6. The medical observation apparatus according to claim 4, wherein
a magnitude of the torque acting as a resistance to the external torque increases as a rotational angle of the at least one joint approaches a limit of a movable range.

7. The medical observation apparatus according to claim 4, wherein
a magnitude of the torque acting as a resistance to the external torque changes according to a zoom magnification when the imaging device captures the observation target.

8. The medical observation apparatus according to claim 1, wherein the circuitry is further configured to determine the torque command value based on a restoring force of the at least one joint.

9. The medical observation apparatus according to claim 1, wherein the circuitry is further configured to determine the torque command value based on a disturbance estimate value of the at least one joint.

10. The medical observation apparatus according to claim 1, wherein the circuitry is configured to determine the external torque acting on the at least one joint.

11. The medical observation apparatus according to claim 10, further comprising
a torque sensor;
wherein the circuitry is configured to
determine the external torque by receiving the external torque acting on the at least one joint from the torque sensor; and
determine the control torque in accordance with the external torque.

12. A driving control method comprising:
controlling, by a processor, driving of at least one joint to be controlled by determining a control torque for the at least one joint from among multiple joints in an arm that supports an imaging device that captures a magnified image of an observation target, the arm including multiple links joined to each other by the joints,
receiving a detected external torque acting on the at least one joint,
determining a torque command value based on the control torque and the detected external torque, wherein the torque command value increases as magnification of the observation target increases, and
controlling the driving of the at least one joint based on the torque command value such that the detected external torque acting on the at least one joint according to an operation on the arm is contained in a fixed range.

13. The method according to claim 12, further comprising:
determining the external torque acting on the at least one joint.

14. A medical observation system comprising:
a medical observation apparatus that captures a magnified image of an observation target; and
a display that displays an image of the observation target captured by the medical observation apparatus, wherein
the medical observation apparatus includes
an imaging device that captures an observation target;
an arm that supports the imaging device and includes multiple links joined to each other by multiple joints; and
circuitry configured to:
determine a control torque for at least one joint to be controlled from among the multiple joints;
determine a torque command value based on the control torque and an external torque, wherein the torque command value increases as magnification of the observation target increases; and
control driving of the at least one joint based on the torque command value such that an external torque acting on the at least one joint according to an operation on the arm is within a fixed range.

15. The medical observation apparatus according to claim 14, wherein the circuitry is configured to determine the external torque acting on the at least one joint.

16. A support arm apparatus comprising:
an arm including multiple links joined to each other by multiple joints; and
circuitry configured to
determine a control torque for at least one joint to be controlled from among the multiple joints,
receive a detected external torque acting on the at least one joint,
determine a torque command value based on the control torque, the detected external torque, and a disturbance estimate value of the at least one joint or on a restoring force of the at least one joint, and
control driving of the at least one joint based on the torque command value such that the detected external torque acting on the at least one joint according to an operation on the arm is within a fixed range.

17. The support arm apparatus according to claim 16, wherein the observation target is magnified and the circuitry is configured to increase the torque command value as magnification increases.

18. The support arm apparatus according to claim 16, wherein the circuitry is configured to determine the external torque acting on the at least one joint.

19. The support arm apparatus according to claim 16, wherein the circuitry is further configured to determine the torque command value based on a restoring force of the at least one joint.

20. The support arm apparatus according to claim 16, wherein the circuitry is further configured to determine the torque command value based on a disturbance estimate value of the at least one joint.

* * * * *